(12) United States Patent
Mountz et al.

(10) Patent No.: US 6,383,794 B1
(45) Date of Patent: May 7, 2002

(54) METHODS OF PRODUCING HIGH TITER RECOMBINANT ADENO-ASSOCIATED VIRUS

(75) Inventors: John D. Mountz; Huang-Ge Zhang, both of Birmingham, AL (US)

(73) Assignee: UAB Research Foundation, Birmingham, AL (US)

(*) Notice: Subject to any disclaimer, the term of this patent is extended or adjusted under 35 U.S.C. 154(b) by 0 days.

(21) Appl. No.: 09/379,841

(22) Filed: Aug. 24, 1999

Related U.S. Application Data

(60) Provisional application No. 60/097,666, filed on Aug. 24, 1998.

(51) Int. Cl.[7] .................... C12N 7/01; C12N 15/86; C12N 15/861
(52) U.S. Cl. ................... 435/235.1; 435/320.1
(58) Field of Search ............... 435/235.1, 471, 435/320.1; 424/93.2, 199.1

(56) References Cited

U.S. PATENT DOCUMENTS 5,858,990 A * 1/1999 Walsh .................... 514/44
6,093,570 A * 7/2000 Ferrari et al. ............ 435/457

FOREIGN PATENT DOCUMENTS

WO  95/06743 * 3/1995 ........... C12N/15/86

OTHER PUBLICATIONS

Li et al (J. Virology 71(7): 5236–5243, Jul. 1997).*
Conway et al (J. Virology 71(11):878–8789, Nov. 1997).*
Xiao et al (J. Virology 72(3): 2224–2232, Mar. 1998).*
Yang et al (Human Gene Therapy 9:1929–1937, Sep. 1, 1998.*

* cited by examiner

Primary Examiner—Mary E. Mosher
(74) Attorney, Agent, or Firm—Benjamin Aaron Adler

(57) ABSTRACT

The present invention discloses a method of producing large-scale recombinant adeno-associated virus stocks by infection of cells with at least one recombinant adenovirus vector(s). The vector(s) encode a therapeutic gene flanked by the terminal repeat ends of adeno-associated virus and the adeno-associated virus rep and cap genes. Transfection with two recombinant adenovirus vector(s) instead of two plasmids plus adenovirus results in the large scale, high titer production of recombinant adeno-associated virus with little to no contaminating adenovirus present.

11 Claims, 22 Drawing Sheets

Hybrid AdAAV

Step 1. 4.7 Kb of PVUII fragment containing both AAVITRs was ligated to BssHII site of pBluescript SK- with a polylinker Step 2. Insertion of GFP expression cassette to replace AAV encoding sequence Step 3. BglII cut GFP expression cassette flanked by AAV ITRs and inserted into pshuttle Step 4. Production of pAdrAVV-GFP in bacterial BJ5183

METHODS OF PRODUCING HIGH TITER RECOMBINANT ADENO-ASSOCIATED VIRUS

CROSS-REFERENCE TO RELATED APPLICATION

This application claims benefit of priority under 35 USC §119(e) of U.S. provisional application Ser. No. 60/097,666 filed Aug. 24, 1998.

FEDERAL FUNDING LEGEND

This invention was produced in part using funds obtained through grant R01-AR42547 and AR-6-2224 from the National Institutes of Health. Consequently, the federal government has certain rights in this invention.

BACKGROUND OF THE INVENTION

1. Field of the Invention

The present invention relates generally to vectors used in gene therapy. More specifically, the present invention relates to adeno-associated viruses and methods of producing said virus.

2. Description of the Related Art

Adeno-associated virus (AAV) is a single-stranded DNA virus of the family of Parvoviridae that has promising features as a vector for gene therapy. First, recombinant adeno-associated virus (rAAV) vectors can transduce terminally differentiated and non-dividing cells. Second, the lack of any apparent pathogenicity, low immunogenicity, relatively high stability of transgene expression, and the potential of targeted integration makes the rAAV superior over adenovirus and other viruses currently used in gene therapy trials. Last, a diversity of studies indicates that rAAV may provide a broad range of clinical applications to treat diseases including neurologic diseases, cancers and inherited monogenic defects, such as beta-thalassemia, sickle cell anemia, Fanconi anemia, chronic granulomatous disease, Gaucher disease, metachromatic leukodystrophy and cystic fibrosis, as well as acquired diseases, such as HIV infection and non-Hodgkin lymphoma.

The major limitation facing practical development of rAAV gene therapy is the difficulty in producing high titer rAAV. There are several factors which affect the ability to produce rAAV a t high titer, including transfection of the AAV genes (cap, rep and therapeutic genes) into host cells (4, 5), obtaining the optimal molar ratio of AAV DNA to helper adenovirus (6, 7, 8), and regulation between AAV rep and cap gene expression (9, 10, 11).

Recombinant adeno-associated virus (rAAV) is currently produced by transfecting cells with two constructs: the rAAV vector plasmid and the rep-cap plasmid. After subsequent adenoviral infection, which is required for rAAV replication and assembly, the virus is purified by CsCl gradients from total cell lygates (12, 13, 14). Because of the low efficiency of DNA transfection, it has previously been impossible to generate high titer rAAV (8, 15, 16, 17, 18, 19, 20).

As stated above, one of the limitations affecting the production of rAAV is determining the optimal molar ratio of the transfected AAV DNA and the Ad helper adenovirus. Pre-infection of host 293 cell with helper adenovirus and/or increasing the dose of helper adenovirus leads to a slight increase in the titer of rAAV (8). However, because adenovirus is cytolytic to 293 cells, it is not possible to achieve optimal production of rAAV before the cells are lysed by the adenovirus.

Regulation of the relative efficiency of the AAV rep and cap gene expression has been shown to significantly affect the production of rAAV. Overexpression of AAV rep78/68 proteins by substituting the p5 promoter with a strong heterologous promoter resulted in considerably lower yields of rAAV (6, 9, 10). In contrast, reduction of rep78/68 protein expression by using attenuated translation initiation codon ACG has resulted in much higher yields of rAAV (11). Replacement of the AAV p40 promoter with the strong cytomygalovirus early promoter can also lead to higher rAAV production (21).

A number of Ad genes, including the E1a, E1b, E2a, E4, and VAI RNA genes, are required for rAAV production (22, 23, 24, 25). The E1a gene product gerves as a transactivator, which leads to up-regulation of the transcriptional activity of numerous Ad genes, as well as the AAV rep and cap genes (22, 23). By interacting with E4, the E1b gene can facilitate the transport of viral mRNAs (25). The E4 gene, particularly open reading frame 6, is involved in facilitating AAV DNA replication. E2a and VAI RNA act to enhance the viral mRNA stability and the efficiency of translation, especially for AAV cap transcripts (25, 26). Two groups have demonstrated that the use of an adenoviral mini-plasmid containing only genes essential for rAAV provides sufficient helper function for growth of rAAV, resulting in relatively high titer rAAV (4, 6, 7). However, a large scale production of rAAV has not been successful because existing methods depend on low efficiency DNA transfection.

The Loxp sequence consists of two 13-bp inverted repeats separated by an 8-bp spacer (27). Cre recombinase can efficiently excise a sequence flanked by Loxp on both sides. Recently, the Loxp/Cre system has been successfully used to conditionally express a cytotoxic gene (26) and to control packaging of adenovirus (29, 30, 31). The conditional-packaging Ad helper virus grows as an E1 deleted adenovirus in 293 cells, but no virion is produced when this virus is grown in 293 cells that express Cre, since the Ad packaging sequence is flanked by Loxp and therefore, excised by the Cre protein. This virus still provides all functions for mini-AdAAV and mini-AdrAAV viral particle formation.

Thus, the prior art is deficient in efficient methods of high titer and large scale production of rAAV. The present invention fulfills this long-standing need and desire in the art.

SUMMARY OF THE INVENTION

The present invention discloses a method of producing large-scale rAAV stocks using co-infection of two recombinant adenoviruses. One encodes the GFP marker gene flanked by the terminal repeat ends of AAV, and the other encodes the AAV rep and cap genes. After heat inactivation of adenovirus, $1 \times 10^{10}$ efu/ml of rAAV-GFP were produced. To compare with conventional two plasmid co-transfection methods, $10^5$ more rAAV can easily be produced with the novel method described herein. Two major improvements over previous methods are introduced in the present invention: (i) construction of recombinant AdAAV encoding rep and cap was done by DNA homologous recombination in bacterial hosts to avoid difficult generation of AdAAV in eukaryotic cells, and (ii) co-transfection of two recombinant adenoviruses instead of two plasmids plus adenovirus resulted in the possibility of large scale production of rAAV.

One object of the present invention is to provide a method of large-scale production resulting in high titers of rAAV using two recombinant adenoviruses instead of using an AAV plasmid to transmit the AAV genes into host cells.

In an embodiment of the present invention, there is provided a method of producing high titers of recombinant adeno-associated virus comprising a therapeutic gene (rAAV-Th), comprising the steps of: a) infecting cells with: (i) a recombinant helper adenovirus (AdAAV), wherein the AdAAV comprises an E1-deleted adenovirus genome, wherein the AdAAV comprises adeno-associated virus (AAV) rep and cap genes; and (ii) a recombinant adenovirus (AdrAVV-Th), wherein the recombinant adenovirus comprises a therapeutic gene (Th), wherein the Th is flanked by AAV ITR ends; b) purifying and titering viral particles from the cells, wherein the viral particles comprise recombinant AAV comprising the therapeutic gene (rAAV-Th), wherein high titers of the rAAV-Th are produced.

In another embodiment of the present invention, there is provided a method of producing high titers of recombinant adeno-associated virus comprising a therapeutic gene (rAAV-Th), comprising the steps of: a) infecting cells with: (i) a conditional-packageable adenoviral helper (hAd) vector, wherein the hAd vector comprises genes encoding adenoviral packaging functions, wherein the genes encoding the packaging functions are flanked by Loxp sequences; (ii) at least one recombinant adeno-associated virus vector, wherein the recombinant adeno-associated virus vector comprises adeno-associated virus (AAV) genes encoding rep and cap proteins, wherein the recombinant adeno-associated virus vector comprises a therapeutic gene (Th), wherein the therapeutic gene is flanked by adeno-associated virus (AAV) inverted terminal repeat (ITR) ends, and wherein the recombinant adeno-associated virus vector lacks genes encoding adenoviral packaging functions; whereby the infection produces adenoviral particles comprising a recombinant adeno-associated virus comprising the therapeutic gene (rAAV-Th); and b) purifying and titering the rAAV-Th, wherein high titers of the rAAV-Th are produced. When the conditional-packaging adenoviral helper vector comprises a gene encoding herpes simplex virus thymidine kinase, the above-described method may further comprise the step of: treating the infected cells with ganciclovir, whereby the treatment reduces contamination of the adenoviral particles by the conditional-packaging adenoviral helper vector.

In still yet another embodiment of the present invention, there is provided a recombinant adeno-associated virus (AdAAV), wherein the AdAAV comprises an E1-deleted adenovirus genome, wherein the AdAAV comprises adeno-associated virus (AAV) rep and cap genes. Furthermore, a mini-recombinant adeno-associated virus may be produced in which the adenovirus genome is deleted for all coding sequences other than those genes required for adeno-associated viral replication.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 4C shows the AdrAAV-GFP expression of green fluorescent protein. One μg of pAdAAV was transfected into 293 cells using lipofectin. The plaque was observed at day 5(a) and day 6(b) post-transfection.

FIG. 7A shows that a stable 293CreNS cell can produce 38 kd Cre protein. 293 cells (1×10$^5$) were transfected with pcDNA3CreNS and lysed with nuclear protein extraction buffer. 100 μg of total protein was loaded onto a 12% gradient polyacrylamide gel. After electrophoresis, the protein was transferred to nitrocellulose and detected with mouse anti-Cre antibody (1:1000 dilution, Babco Berkeley Antibody Company), followed by an HRP conjugated goat anti-mouse antibody. The ECL kit (Amersham) was used to develop the blot. Lane 1, 293 control cells; Lane 2, 293CreNS cell.

DETAILED DESCRIPTION OF THE INVENTION

Figure 1A:
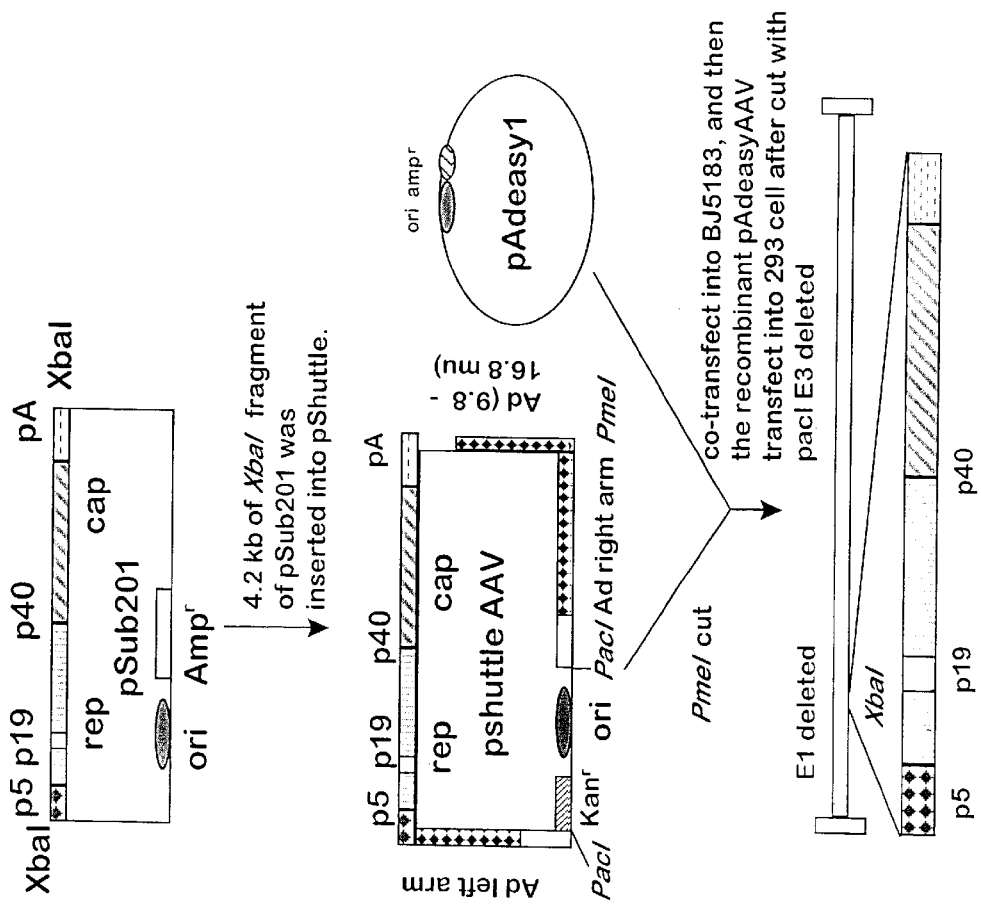
FIG. 1A shows the construction of hybrid AdAAV. The XbaI fragment encoding AAV rep and cap genes was excised from the AAV psub201, and inserted into the XbaI site of pShuttle. After linearization with PmeI, 1 μg of pShuttle-AAV was mixed with pAdeasy1, and co-transformed into BJ5183 cells. The correct recombinant pAdAAV was identified by restriction enzyme digestion. The P5 promoter drives rep78 and rep68 and the p 19 promoter drives rep52 and rep40. P40 promoter drives expression of the cap gene.

This invention entails high titer production of AAV by a unique method of coinfecting eukaryotic cells with two novel AAV and AdAAV constructs. AAV is an extremely appealing vector for gene therapy. This important advance in production of significantly higher titers of AAV exceeds previous methodologies both in practicality and in production of viral particles. Previous techniques use homologous in vivo recombination which is time consuming and yields the correct recombinant at very low frequencies. In addition, AAV requires the presence of adenovirus for production resulting in some contamination with adenovirus and also very low titers of AAV. The AdAAV has been engineered to produce only AAV, but not package adenovirus, and also produces AAV with titers of 10$^7$ T.U./mL compared to previous titers of approximately 10$^4$ T.U./ml. This invention uses two novel adenovirus-based constructs that carry essential AAV genes and the desired therapeutic gene. With the potential market for gene therapy, this technique along with the novel constructs may provide the necessary tools for successful gene therapy regimens in the treatment of numerous inherited genetic disorders and acquired diseases.

There are many different applications of the instant invention. For example in vector production in gene therapy for cancer and certain monogenic defects such as beta-thalassemia, sickle cell anemia, Fanconi anemia, chronic granulomatous disease, Gaucher disease, metachromatic leukodystrophy and cystic fibrosis and in vector production in gene therapy for acquired diseases such as non-Hodgkin's lymphoma, human immunodeficiency virus infection, etc. Further, the methods described herein may be used in vitro expression system for high production of specific proteins of interest.

The present invention discloses a hybrid AdAAV which enables high titer and large scale production of rAAV free of Ad helper virus. Hybrid AdAAVs are capable of delivering all of the genetic components for high titer rAAV production, as well as minimizing contamination of Ad helper virus. The data shown herein demonstrates that hybrid AdAAVs, which express the AAV rep and cap genes and a marker gene flanked by the AAV ITR, can be generated by homologous DNA recombination in a bacterial host and used to produce high titer recombinant AdAAV in 293 cells. Previous investigators have failed to generate recombinant AdAAV by direct DNA homologous recombination in 293 cells. This was probably due to an inhibition of adenovirus replication by AAV rep (1, 2, 3). Results presented herein are the first to demonstrate that the replication of hybrid AdAAV is not inhibited by expression of rep, and that the viral titer is not significantly different from E1 deleted recombinant AdCMVlacZ virus.

The present invention discloses novel strategies to allow production of high titer and Ad free rAAV by adjusting the ratios of two recombinant adenoviruses, one expressing AAV rep and cap proteins and the other expressing the therapeutic gene flanked by AAV ITR. Utilization of the Loxp/Cre system combined with TK drug selection demonstrated that Ad helper-free rAAV can be produced. The results herein demonstrate that sufficient titers of rAAV can be provided for clinical application. The cost of production of this rAAV will be lower since higher transfection efficiency and titers mean that fewer cells are required for growth.

The present invention is also directed towards a method of producing large scale preparations containing high titers of uncontaminated recombinant adeno-associated virus.

The present invention is directed towards a method of producing high titers of recombinant adeno-associated virus comprising a therapeutic gene (rAAV-Th), comprising the steps of: a) infecting cells with: (i) a recombinant helper adenovirus (AdAAV), wherein the AdAAV comprises an E1-deleted adenovirus genome, wherein the AdAAV comprises adeno-associated virus (AAV) rep and cap genes; and (ii) a recombinant adenovirus (AdrAVV-Th), wherein the recombinant adenovirus comprises a therapeutic gene (Th), wherein the Th is flanked by AAV ITR ends; b) purifying and titering viral particles from the cells, wherein the viral particles comprise recombinant AAV comprising the therapeutic gene (rAAV-Th), wherein high titers of the rAAV-Th are produced.

Representative cells include 293 cells and 911 cells. Preferably, the adenovirus genome is deleted for all coding sequences other than those genes required for adenoviral replication. More preferably, the genes required for adenoviral replication, and hence remaining on the adenoviral genome, are E1A, E1B, E2A, E4 and VIA. The above-described method may further comprise the step of: inactivating the AdrAAV-Th without inactivating the rAAV-Th, wherein the inactivating is performed prior to the purifying and titering the rAAV-Th. Typical methods of inactivation are multiple cycles of freezing and thawing the cells and/or heating to about 56° C. for about 1 hour.

The present invention is further directed towards a method of producing high titers of recombinant adeno-associated virus comprising a therapeutic gene (rAAV-Th), comprising the steps of: a) infecting cells with: (i) a conditional-packageable adenoviral helper (hAd) vector, wherein the hAd vector comprises genes encoding adenoviral packaging functions, wherein the genes encoding the packaging functions are flanked by Loxp sequences; (ii) at least one recombinant adeno-associated virus vector, wherein the recombinant adeno-associated virus vector comprises adeno-associated virus (AAV) genes encoding rep and cap proteins, wherein the recombinant adeno-associated virus vector comprises a therapeutic gene (Th), wherein the therapeutic gene is flanked by adeno-associated virus (AAV) inverted terminal repeat (ITR) ends, and wherein the recombinant adeno-associated virus vector lacks genes encoding adenoviral packaging functions; whereby the infection produces adenoviral particles comprising a recombinant adeno-associated virus comprising the therapeutic gene (rAAV-Th); and b) purifying and titering the rAAV-Th, wherein high titers of the rAAV-Th are produced.

Representative cells are 293CreNS cells. Generally, the packaging functions comprise genes encoding hexon protein, penton protein, core protein and DNA polymerase. Preferably, the conditional-packaging adenoviral helper vector comprises a gene encoding herpes simplex virus thymidine kinase, and if so, the above-described method may further comprise the step of: treating the infected cells with ganciclovir, whereby the treatment reduces contamination of the viral particles by the conditional-packaging adenoviral helper vector.

Representative therapeutic genes include an HSV-TK gene, a gene encoding GFP and genes encoding proteins that direct and/or regulate apoptosis. Preferably, the genes encoding proteins that direct and/or regulate apoptogig include Bax, Bad, IkB-DN, FasL and Akt. Typically, the above-described purification is performed by $CsCl_2$ gradient centrifugation.

Additionally, the present invention provides for the above-described methods in which the translation of the gene encoding the rep protein is attenuated, preferably by changing the start codon of the gene, more preferably by changing the start codon from ATG to ACG. Furthermore, the present invention provides for the above-described methods in which the expression of the gene encoding the cap protein is increased over endogenous levels. Preferably, the expression of the cap gene is increased by replacing a promoter directing expression of the gene, and more preferably, wherein a p40 promoter directing expression of the gene encoding the cap protein is replaced with a chicken β-actin promoter comprising an HCMV enhancer. The above-described methods may further include situations in which the AAV gene encoding the cap protein is engineered such that the rAAV-Th is targeted to a specific cell type expressing a specific ligand, such as a CD4 binding domain of the gp120 AIDS capsid or an RGD binding motif.

Generally, the above-described methods are used to treat an individual in need of such treatment, preferably for a purpose selected from the group consisting of therapy, diagnosis, disease monitoring and disease imaging.

The present invention also provides for a recombinant adeno-associated virus (AdAAV), wherein the AdAAV comprises an adenovirus genome, wherein the AdAAV comprises adeno-associated virus (AAV) rep and cap genes, wherein the AAV rep and cap genes are flanked by AAV inverted terminal repeat (ITR) ends. Preferably, the adenovirus genome is deleted for all coding sequences other than those genes required for adenoviral replication, and more preferably, the genes required for adenoviral replication that remain in the adenoviral genome are E1, E2A, E4 and VIA.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1995)]: "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence. "Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. One preferred embodiment is the use of a vectors containing coding sequences for the gene for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of a gene in transgenic systems, in accordance with conventional Southern hybridization techniques known to those of ordinary skill in the art. Both the Northern blot and Southern blot use a hybridization probe, e.g. radiolabelled cDNA or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

U.S. Pat. Nos. 3,654,090, 3,850,752, and 4,016,043 are referred to by way of example for their disclosure of alternate labeling material and methods.

As used herein, the term "high titer" is defined as transduction units of recombinant AAVGFP or AAVLacZ.

As used herein, the term "recombinant adeno-associated virus" refers to AAV rep and cap genes replaced by a marker or therapeutic genes.

As used herein, the terms "rep" and "cap" refer to the genes AAV encoding the rep and cap proteins.

As used herein, the terms "E-1-deleted and E3-deleted" refer to adenovirus 5 with deletions of the E1 and E3 genes.

As used herein, the term "attenuated" refers to a method of regulating gene expression by controlling the amount of transcription initiation by RNA polymerase.

As used herein, the term "conditional-packageable" adenoviral helper vector refers to packaging signal of adenovirus flanked by loxp sites. This virus can not be packaged without the presence of the cre protein.

The following examples are given for the purpose of illustrating various embodiments of the invention and are not meant to limit the present invention in any fashion.

Figure 1B:
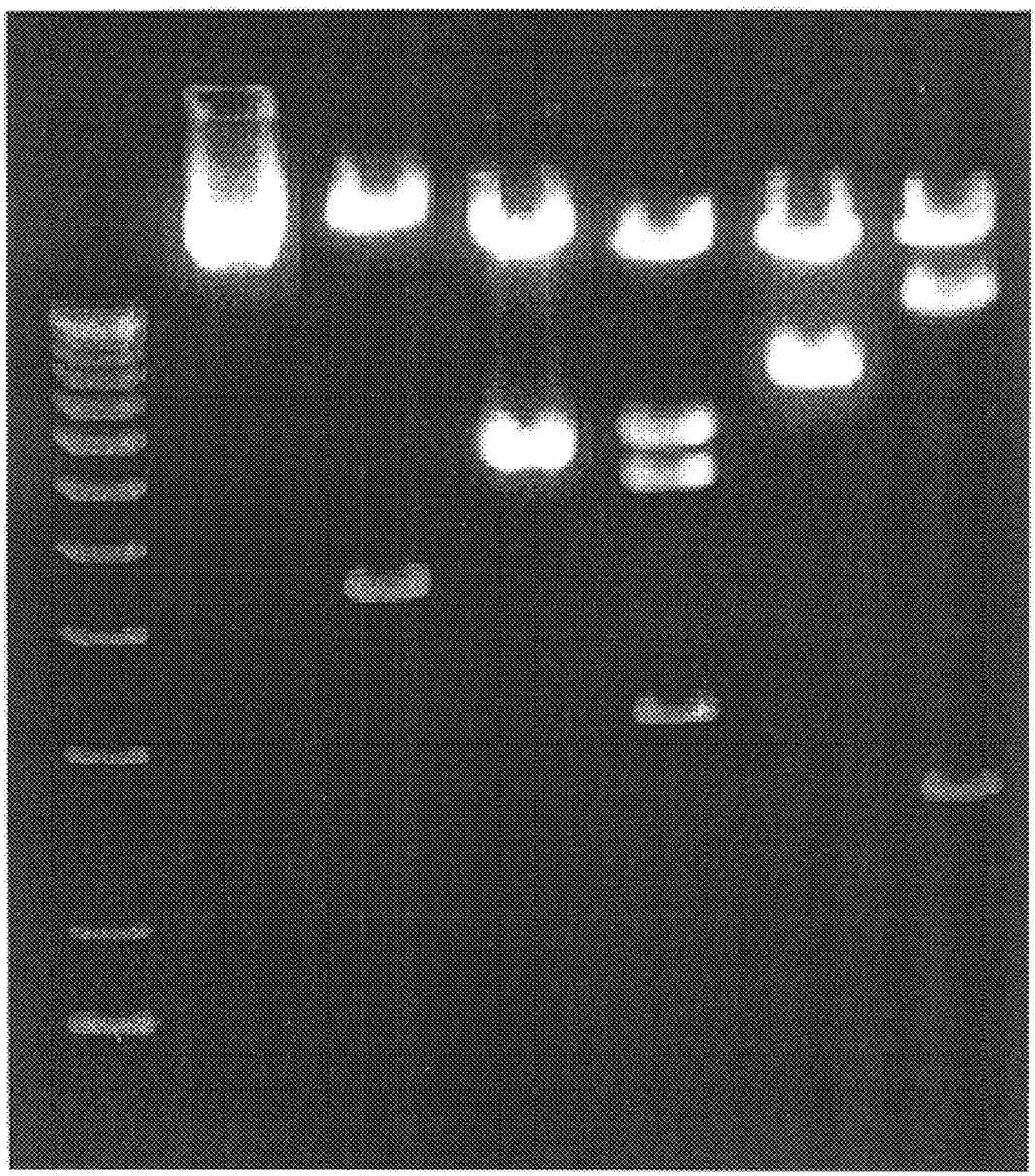
FIG. 1B shows the XbaI, SalI and EcoRI restriction maps of recombinant pAdAAV DNA. 10 μg of plasmid pAdAAV DNA or pAdeasy1 were cut with XbaI, SalI or EcoRI. After digestion for 1 hour at 37° C., the samples were electrophoresed on a 1% agarose gel and photographed under UV light. Lane 1, 1kb ladder (BRL); Lane 2, 3, PAdeasy1, pAdAAV digested with XbaI, respectively; Lane 4, 5, Padeasy1, pAdAAV digested with SalI, respectively; Lane 6, 7, pAdeasy1, pAdAAV digested with EcoRI, respectively.

EXAMPLE 1
Construction of the Recombinant Plasmid pAdeasy1 AAV in a Bacterial Host The 4.2 kb XbaI fragment of AAV pSub201 (12, 17) containing the AAV rep and cap genes was cloned into ΔE1 XbaI site of an adenoviral shuttle vector, pShuttle (32, provided by Bert Vogelstein, Baltimore, Md.) (FIG. 1A). The resultant construct (pShuttleAAV) was then linearized with PmeI. pAdAAV recombinant plasmid DNA was constructed by mixing 1 μg of pShuttleAAV with pAdEasy-1 and electroporated into competent cell BJ5183. The correct recombinant clone was identified by restriction enzyme digestion. After digestion with XbaI, SalI and EcoRI, restriction enzyme products were mapped (FIG. 1B).

EXAMPLE 2
pAdAAV can Express AAV Rep and Cap mRNA

Figure 2:
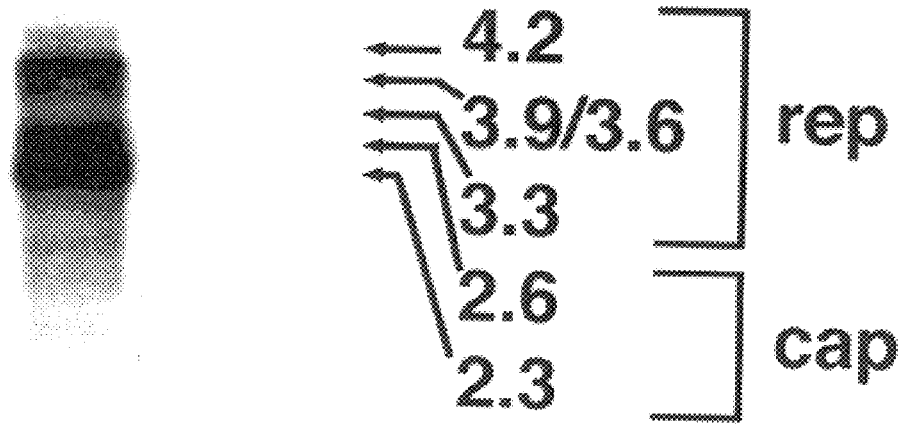
FIG. 2 shows that a hybrid AdAAV can express AAV rep and cap genes. 10 μg of total RNA extracted from AdAAV-infected 293 cells was transferred onto a nylon membrane and hybridized with $\alpha$-$^{32}$P labeled AAV probe (nt position from 2202 to 4344 bp). The film was exposed for 2 hours. Lane 1, RNA marker (BRL); Lane 2, total RNA extracted from 293 cells infected with AdCMVLacZ (5 pfu/cell); Lane 3, total RNA extracted from 293 cells infected with AdAAV (5 pfu/cell); Lane 4, total RNA from 293 cells.

One μg of pAdAAV was cut with PacI to release full length pAdAAV DNA. After transfection into 293 cells, numerous plaques formed by day 12. To determine if AAV rep and cap genes were expressed, RNA was produced from the cells and analyzed by northern blot analysis. The blot was hybridized with a α-$^{32}$P labeled AAV fragment (2202–4344 bp). All AAV transcripts were detected at 16 hours postinfection. Hybridization bands at approximately 2.3 and 2.6 kb related to cap mRNAs and bands at 3.3, 3.6, 3.9 and 4.2 kb related to rep RNA species were observed (FIG. 2).

Figure 3:
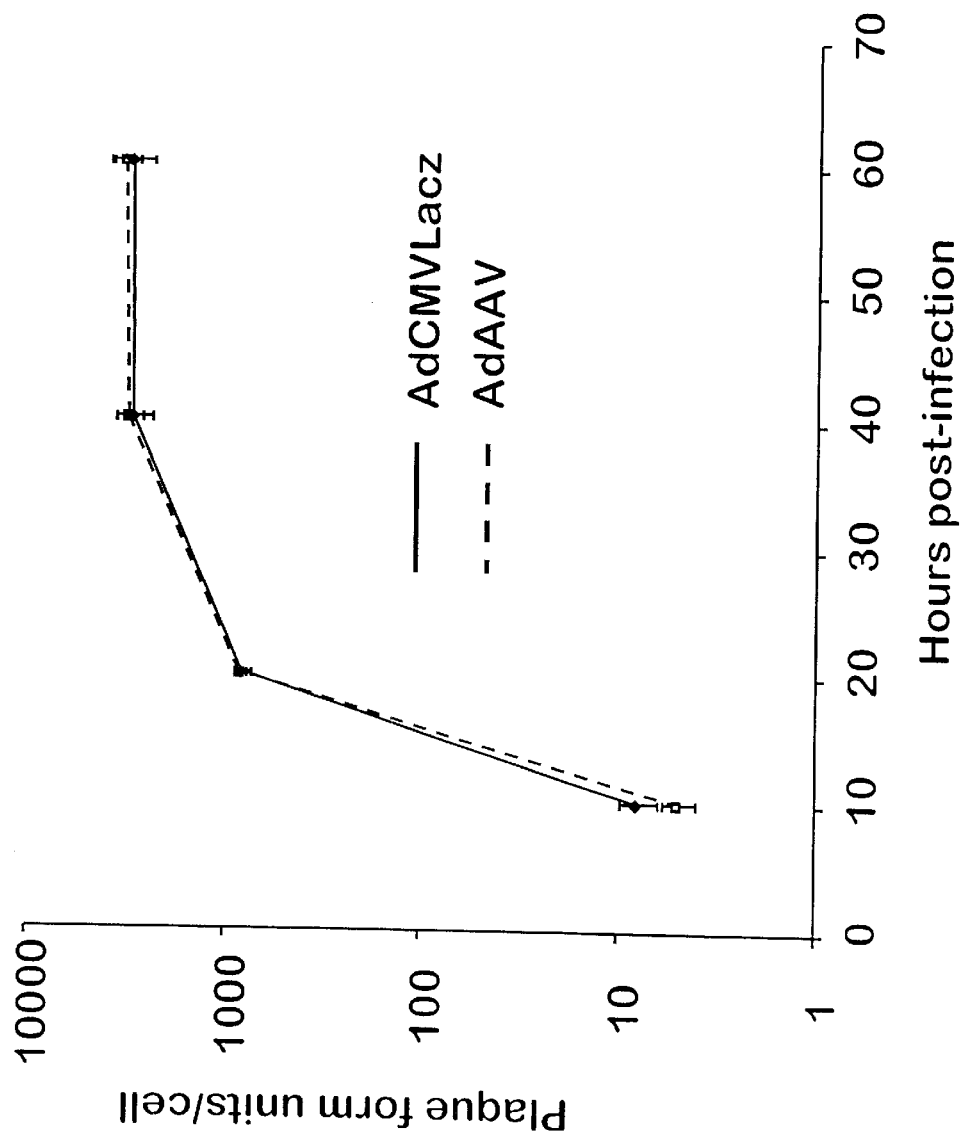
FIG. 3 shows high titer production of a hybrid AdAAV. CsCl purified AdAAV or AdCMVLacZ was used to infect 293 cells at a dose of 10 pfu/cell. The cells were infected in triplicate in 6-well plates. The cell pellets were collected after culture for 10, 20, 40, and 60 hours. The pellets were frozen and thawed three times before titration. The virus was titrated by 10-fold dilutions of harvested stock. The number of plaques was read at 48 hour post-infection and viral titer expressed as plaque forming units/cell.

EXAMPLE 3
Expression of AAV Genes in a AdAAV Hybrid Vector is not Cytotoxic to 293 Cells Previous investigators have proposed that expression of AAV rep genes might be toxic to cells, and construction of AdAAV viral particles may be not possible in a eukaryotic host cell. In contrast, pAdAAV can produce both cap and rep mRNAs (FIG. 2) which has no effect on production of AdAAV (FIG. 3). This result indicates that the previous failure to produce AdAAV viral particles may have been due to unidentified factor(s) that interfere with Ad-AAV DNA recombination in 293 cells, but do not affect cell survival after such recombination occurs.

EXAMPLE 4
Production of AdrAAV-GFP

Figure 4A:
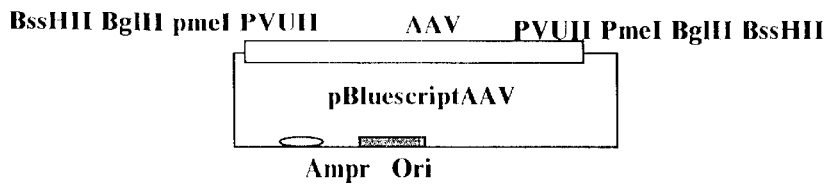
FIG. 4A shows the construction of pAdrAAV-GFP. Construction of pAdrAAV-GFP was carried out as described in the examples.
Figure 4A:
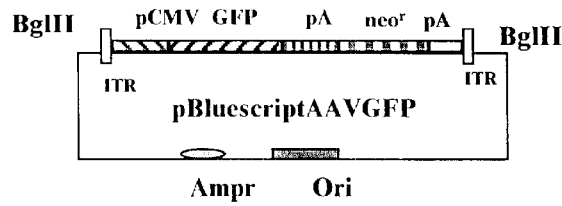
Figure 4A:
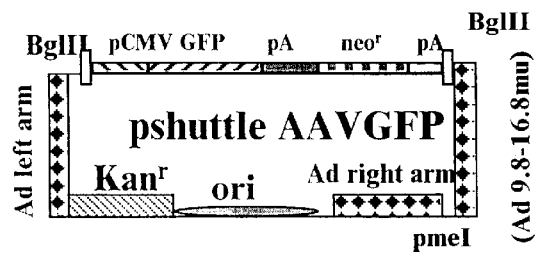
Figure 4A:
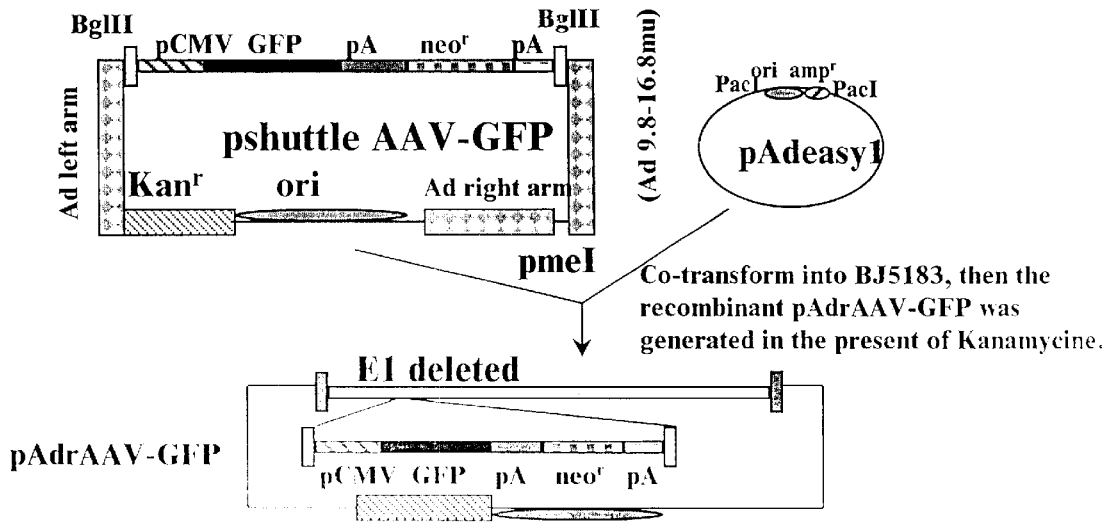
Figure 4B:
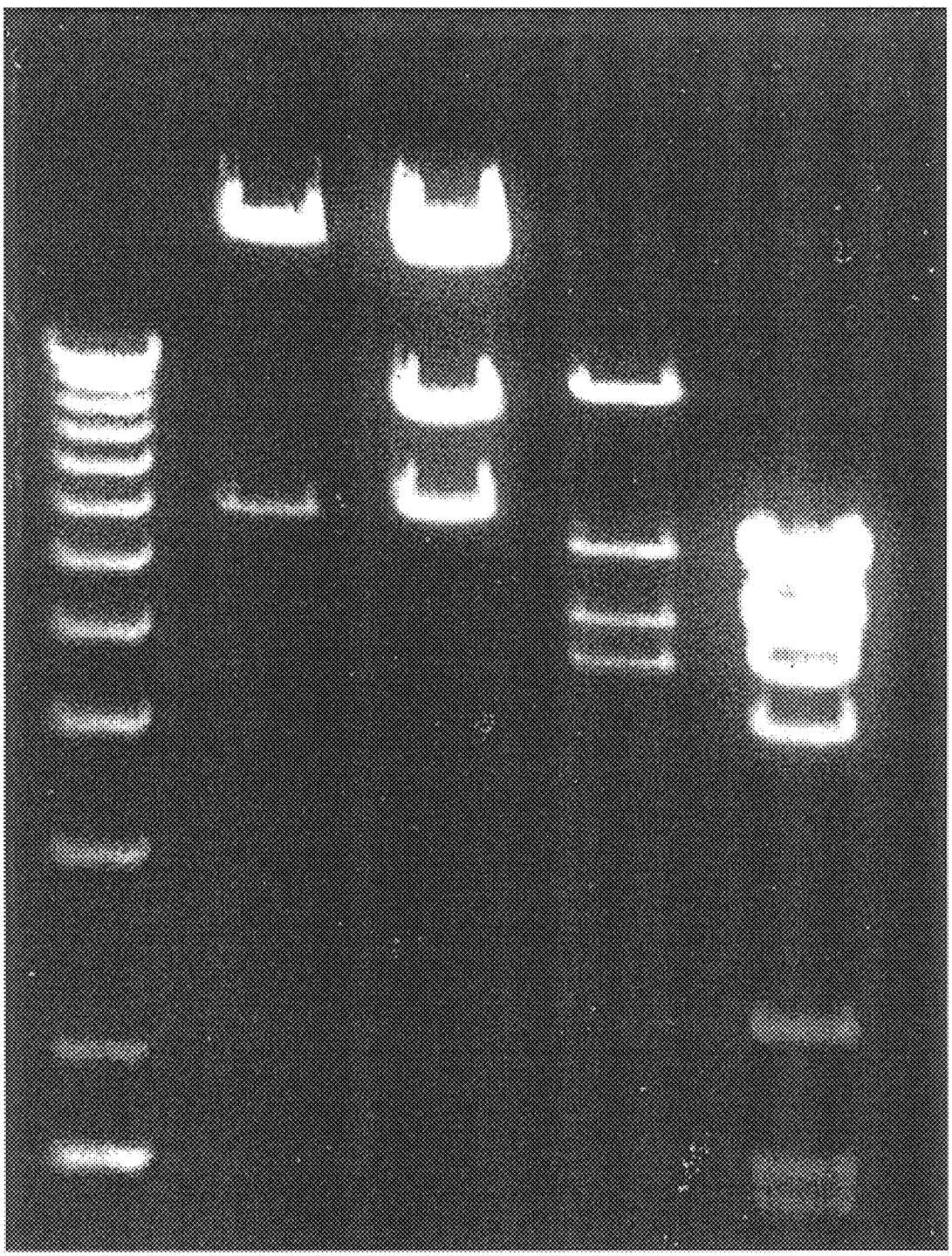
FIG. 4B shows the SalI and BglII restriction maps of pAdrAAV-GFP. 10 μg of either pAdeasy1 or pAdrAAV-GFP were digested with SalI or BglII. The digested DNAs were eletrophoresed on a 1% agarose gel. Lane 1, 1 kb ladder (BRL); Lane 2, 3, SalI digested pAdeasy1, pAdrAAV-GFP, respectively; Lane 4, 5, BglII digested pAdeasy1, pAdrAAV-GFP, respectively.

The PvuII fragment of psub201, which contains wild-type AAV genes flanked by AAV ITR, was inserted into pBluescript SK- (Strategene) as showed in FIG. 4A. pBlueScriptSKrAAVGFP was constructed by replacing the AAV encoding sequencing (between the AAV ITR sequences) with GFP (CLONTECH) driven by the CMV promoter from pcDNA3. The pAdrAAV-GFP recombinant plasmid was constructed by excising the GFP expression unit flanked by AAV ITR with BglII and ligating the resultant rAAV-GFP fragment into the BglII site of the pShuttle vector (32). Selection of recombinants and production of AdrAAV-GFP was subsequently carried out (32). The insertion of rAAV-GFP into the E1 deleted locus was checked by partial sequence analysis of the flanking region and by restriction enzyme analysis (FIG. 4B), and expression of GFP was confirmed by fluorescent light microscopy (FIG. 4C).

EXAMPLE 5
Production of rAAV-GFP by Co-infection with AdAAV and AdrAAV-GFP

Figure 5:
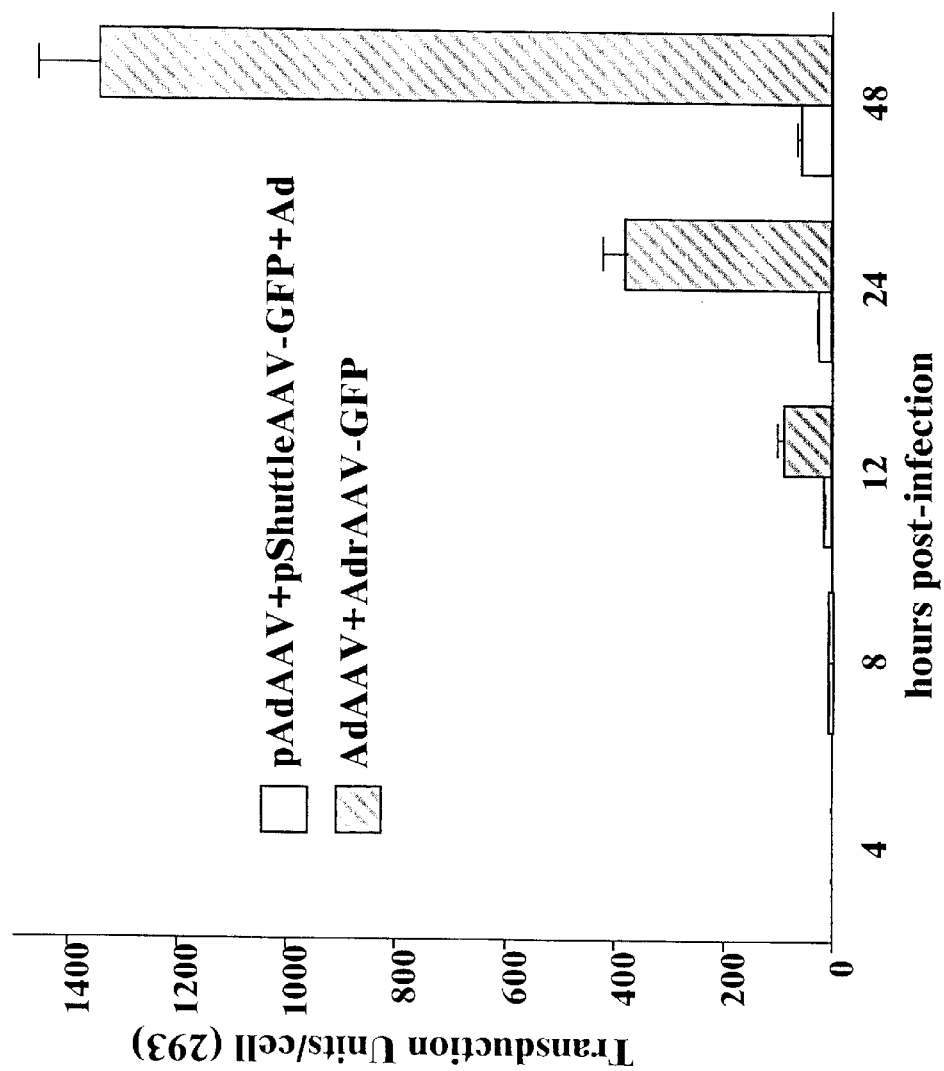
FIG. 5 shows high titer production of rAAV-GFP using two recombinant adenoviruses. The rAAV-GFP was produced and titrated. The open bar represents the titer of rAAV-GFP using two plasmid DNA followed by adenovirus (5 pfu/cell) infection. The solid hatched bar represents the titer of rAAV-GFP using the two recombinant adenovirus method of the present invention.

AdAAV and AdrAAV-GFP viral particles were co-infected at an equal concentration of 5 pfu/cell into 293 cells. This led to lysis of 50% of the cells at 40 hour post-infection. To determine the relative amount of rAAV-GFP, the cells were lysed by freezing and thawing three times and the viral supernatant was heated to 56° C. for 1 hour. This treatment is toxic to AdrAAV-GFP but not to rAAV-GFP. To obtain an accurate titer for rAAV-GFP, and eliminate counting of green cells due to minor contamination by AdrAAV-GFP, CsCl purified rAAV-GFP was first incubated with adenoviral neutralization antibody (1D6.14, provided by Dr. Curiel, 33) at 37° C. for 1 hour, and then inoculated into 293 cells at 10-fold serial dilution. The titer was determined by counting the number of green cells at different dilutions at 48 hour post-infection. The results were expressed as transduction units/cell (T.U./cell). The data indicate that a very high titer of rAAV-GFP (1.5×10$^3$ T.U./cell) can be produced by this method (FIG. 5). This produces rAAV-GFP at a titer approximately 8×10$^2$ higher than titers achieved using co-transfection of rAAV-GFP DNA followed by infection with adenovirus (5 pfu-cell).

Figure 6A:
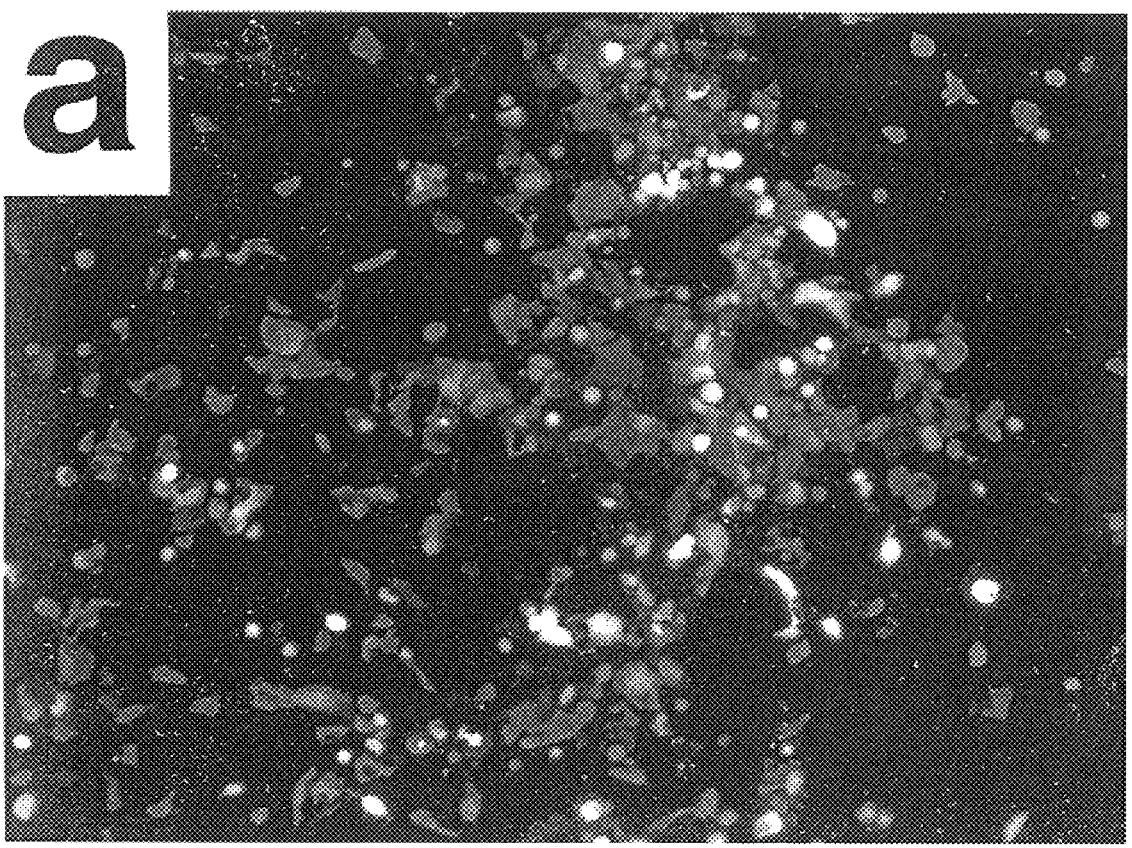
FIG. 6 shows the production of rAAV-GFP by co-infection of AdAAV and pBluescriptKSrAAV-GFP. pBluescriptKSrAAV-GFP was lipofectin transfected into 293 cells, and followed by infection with AdAAV at 1 pfu/cell at 24 hours post-transfection (FIG. 6A). As a control, 293 cells were also co-transfected with pBluescriptKSrAAV-GFP and pAdAAV (provided by Dr. Smauski) followed by adenovirus 5 infection at 1 pfu/cell (FIG. 6B). Photos were taken at 3 days post-infection.
FIG. 6C shows that co-infection of AdAAV and AdrAAV-GFP results in high efficiency replication of rAAV-GFP. 293 cells were co-infected or co-transfected with AdAAV and AdrAAV-GFP or pShuttleAAV-GFP and pAdAAV (12) plus adenovirus dl309, respectively. Low molecular weight DNA was extracted using the Hirts method. The DNA samples were digested with DpnI to eliminate plasmid DNA. 10 μg of extracted DNA was transferred and hybridized with an α-$^{32}$P labeled GFP probe. The film was exposed for 12 hours except lane 4, which was exposed for 1 hour. Lane 1, plasmid pShuttlerAAVGFP; Lane 2, AdAAV+AdrAAV-GFP 10 hour post-infection; Lane 3, PShuttlerAAVGFP+pAdAAV+dl309 10 hour post-infection; Lane 4, AdAAV+AdrAAV-GFP 24 hour post-infection; Lane 5, PShuttlerAAVGFP+pAdAAV+dl309 24 hour post-infection; Lane 6, 293 cell infected with AdCMVlacZ 24 hour post-infection.
Figure 6B:
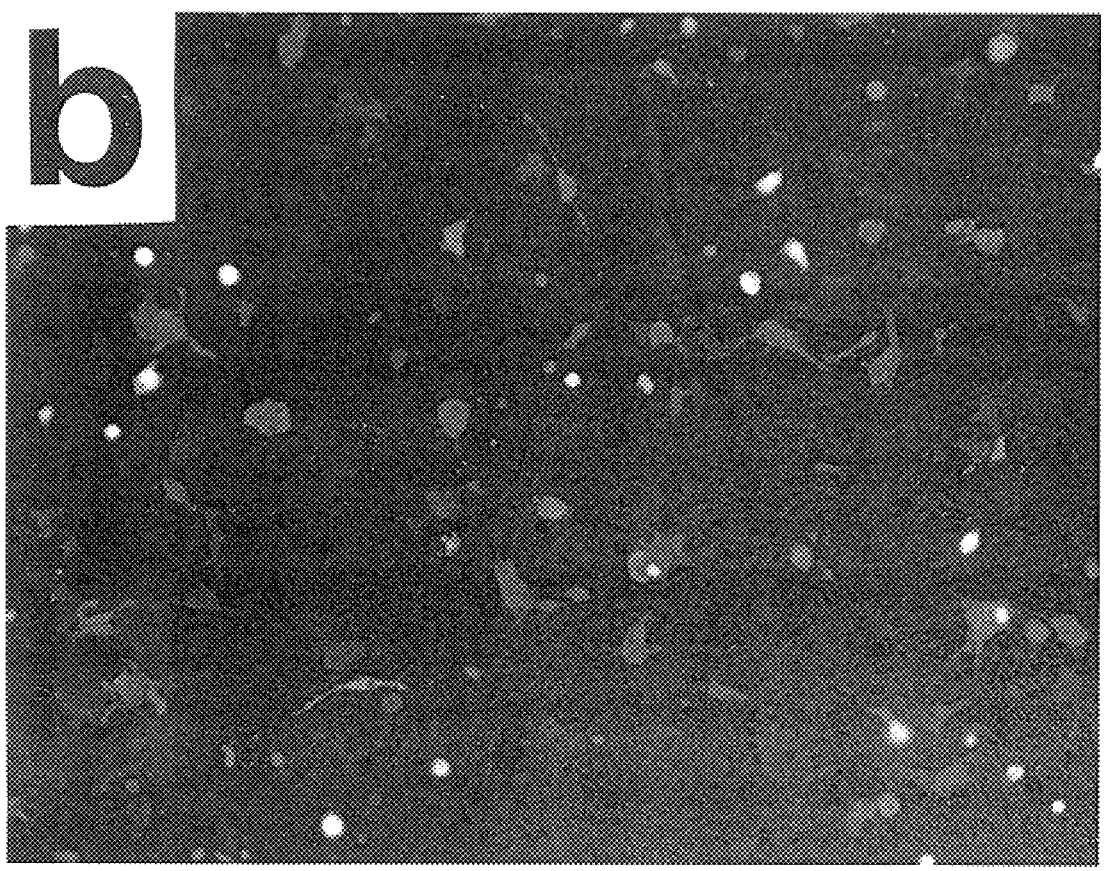

EXAMPLE 6
Co-infection of AdAAV and AdrAAV-GFP Results in High Replicative Efficiency of rAAV-GFP The co-infection of AdAAV and AdrAAV-GFP each at 1 pfu/cell into 293 cells led to 50% cell lysis at 40 hours post-infection. To determine the relative amount of rAAV-GFP, the cells were lysed by freezing and thawing three times and the viral supernatant was heated to 56" C. for 1 hour and purified by CsCl$_2$ centrifugation. This treatment is toxic to AdrAAV-GFP, but not to rAAV-GFP. To obtain accurate rAAV-GFP titer, and avoid miscounting due to minor contaminated AdrAAV-GFP, CsCl purified rAAV-GFP was first incubated with adenoviral neutralization antibody at 37° C. for 1 hour, and then inoculated into HeLa cells at 10-fold serial dilution. The titer was determined by counting the number of green cells at different dilutions 48 hours post-infection. The results indicate that very high titer rAAV-GFP (1×10$^7$ T.U./ml) can be produced by this method. This produces rAAV-GFP at a titer approximately 10$^3$ higher than titers achieved using co-transfection of rAAV DNA followed by infection with adenovirus. To further demonstrate this novel strategy of producing higher titer of rAAV, plasmid pBluescriptKSrAAV-GFP was used to transfect 293 cells followed by infection with AdAAV. At 48 hours post-infection, there were many more green cells than when cells were transfected using two rAAV plasmid DNAs and adenovirus (compare FIGS. 6A and 6B).

Figure 6C:
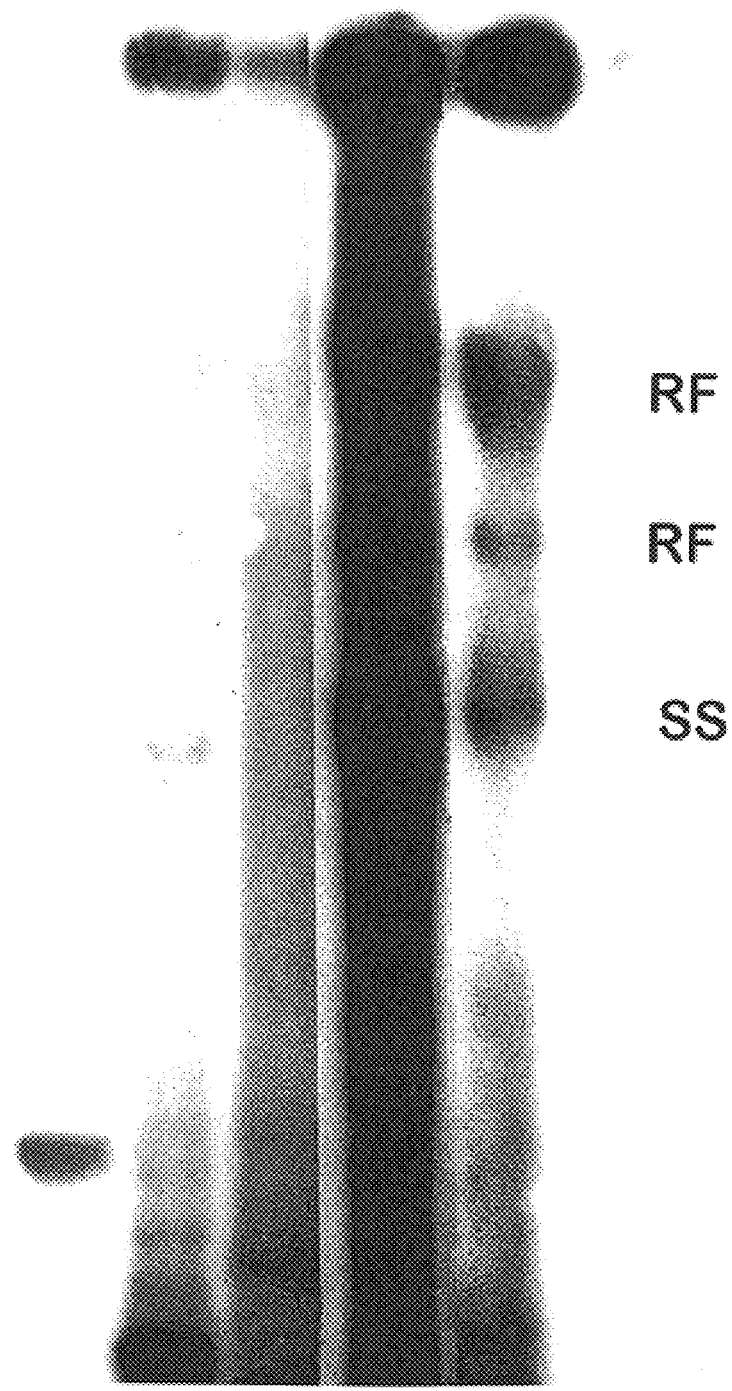

Co-transfection of rAAV-GFP and the AAV rep-cap plasmid DNA results in low replication efficiency of rAAV-GFP. To determine if co-infection of both recombinant adenoviruses can increase the replication efficiency of rAAV-GFP, AdAAV and AdrAAV-GFP viral particles were co-infected into 293 cells (1 pfu/cell of each virus). At 48 hours post-infection, low molecular weight DNA was extracted using the Hirts DNA extraction method (34) and analyzed using an α-$^{32}$P labeled GFP probe. The results demonstrated that co-infection with two recombinant adenoviruses resulted in a greatly increased replication efficiency compared to the DNA co-transfection method (see FIG. 6C, lane 4).

Figure 7A:
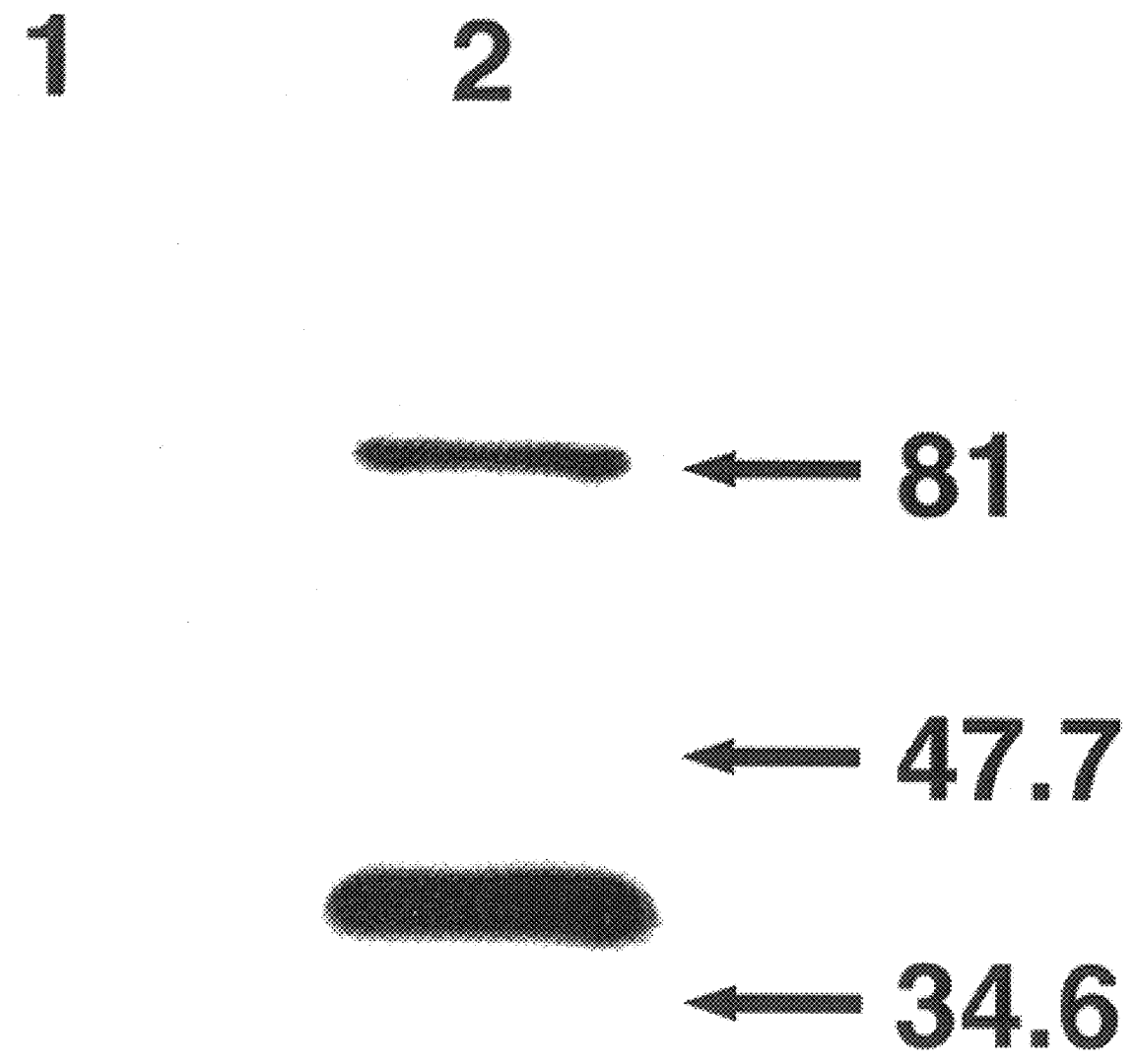
Figure 7B:
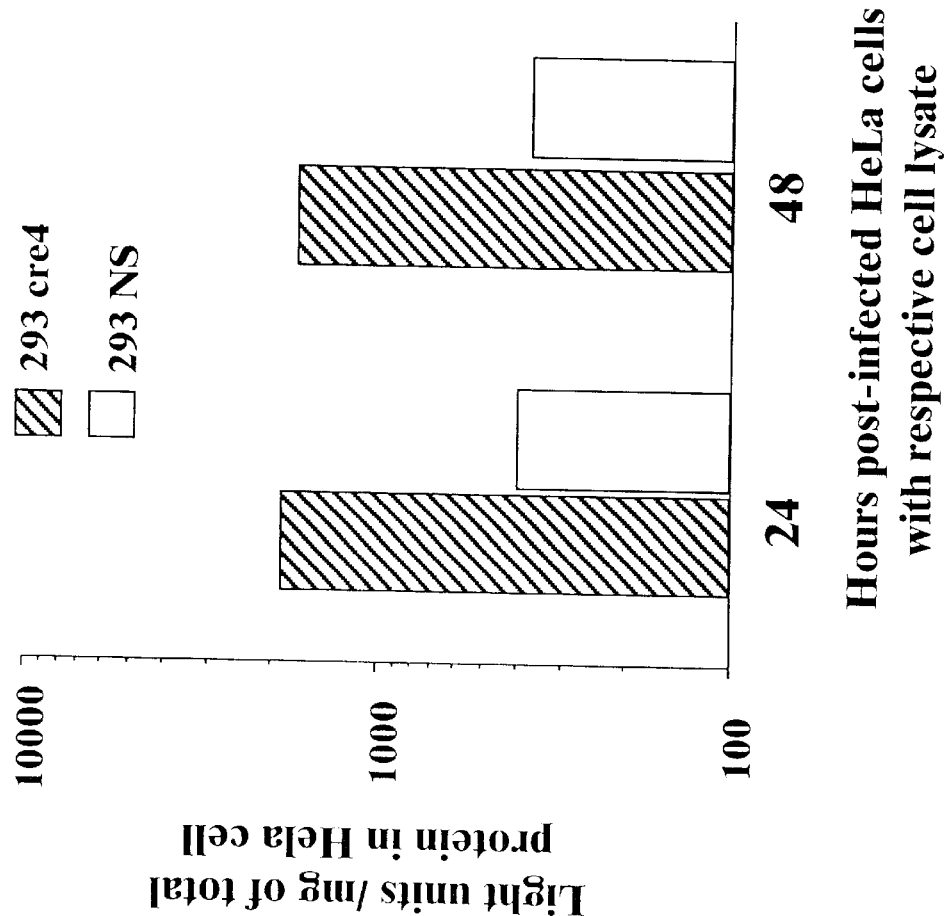
FIG. 7B shows the increased excision efficiency of a Loxp flanked adenoviral packaging signal using 293 cells with stable expression of Cre with a nuclear localization signal. 293CreNS or 293Cre4 (provided by Merck &Co. Inc.) was infected with AdLC8cluc (30) at 1 pfu/cell for 48 hours. The cell lysates were frozen and thawed three times. ⅒ of the volume of supernatant was used to infect Hela cells in a 6-well plate. The cellular extracts were used for analysis of luciferase gene expression. The open and hashed bars present three samples from each treatment.

EXAMPLE 7
Utilization of Loxp/Cre with Nuclear Localization Signal Enables more Efficient Elimination of Ad Conditional Packageable Helper Virus Previous investigators have demonstrated that AdLC8cluc, which contains the Loxp flanked packaging signal, is not efficiently packaged in 293Cre4 because the packaging signal is excised. When transiently expressed from an Ad vector in murine macrophage cells, the Cre recombinase is more efficient at excision of the sequences between Loxp sites located in the Ad genome. The efficiency of Cre-mediated excision is increased by the addition of a nuclear localization signal to Cre (28). Therefore, a 293 cell line with constitutive expression of Cre with a nuclear localization signal was established (FIG. 7A). This results in a reduction of the conditional-packageable Ad helper virus (FIG. 7B). The 293CreNS increases the titer of Ad helper-dependent replicative AdAAV or AdrAAV.

EXAMPLE 8
TK Drug Selection to Eliminate Contamination

Thymydine kinase drug selection is a powerful tool to selectively kill thymydine kinase positive cells. This strategy was used to eliminate minor contamination by the Ad helper virus (AdAAV) from the rAAV-GFP preparation. E1-deleted recombinant adenovirus expressing herpes thymydine kinase gene can be eliminated in 293 cells in the presence of the thymydine kinase analogue, ganciclovir (0.1 mM), but not E1-deleted recombinant at adenovirus expressing GFP (Table 1).

TABLE 1

GCV elimination of AdCMVTK in 293 cells.

| Virus+ | 100 pfu/cell | 10 pfu/cell |
| --- | --- | --- |
| AdCMVTK | 0 | 0 |
| AdCMVGFP | $1.2 \times 10^3$ | $1.8 \times 10^3$ |

+AdCMVTK contains the herpes TK gene regulated by the CMV promoter, and inserted into the E1 region of adenovirus 5 (28). AdCMVGFP contains the GFP gene regulated by the CMV promoter inserted into the Ad E1 region. The numbers in each column represent viral progenies produced in 293 cels in the present of GCV (0.1 mM).

EXAMPLE 9
Optimization of the Ratio and Time of Addition of AdAAV and AdrAAV-GFP to Maximize Yield of rAAV-GFP A central feature of production of adeno-associated virus is that productive infection in cell culture requires co-infection by an adenovirus helper virus. The co-infection stimulates AAV replication and gene expression (26, 35, 36, 37). Previous studies have shown that increasing the dose of helper virus or infecting the host cell in advance can significantly boost the yield of rAAV (8, 21). Because adenovirus is cytolytic to 293 cells, delivery of the rep and cap genes cannot be achieved by either increasing the dose of Ad helper virus or pre-infection with the Ad helper virus. The present system was therefore developed: a recombinant adenovirus expressing AAV rep and cap genes (AdAAV) co-infected with another recombinant E1-deleted adenovirus expressing the GFP gene flanked by AAV ITR (AdrAAV-GFP). This system was used to optimize the time of infection and dose ratio of these two recombinant viruses as indicated in Table 2. In a parallel control experiment, two plasmid DNAs were co-transfected followed by adenovirus infection.

TABLE 2

Optimization of rAAV-GFP production by adjusting the timing of infection and dose ratio between the two recombinant viruses

| Recombinant virus | Time post-infection (hour) | Viral dosage (pfu/cell) |
| --- | --- | --- |
| AdAAV | 0, 0, 0, 0, 0, 1, 2, 4, 8 | 1, 1, 1, 5, 10 |
| AdrAAV-GFP | 0, 1, 2, 4, 8, 0, 0, 0, 0 | 1, 5, 10, 1, 1 |

The effects of treatments were evaluated by analysis of the, rAAV-GFP replication efficiency, titer of rAAV-GFP, and the level of expression of rep and cap. Briefly, to evaluate the replication efficient of rAAV-GFP, the Hirt DNA extraction method (34) was used to isolate low molecular weight DNA, followed by Southern transfer and hybridization using an $\alpha$-$^{32}$P labeled GFP probe. The titration of rAAV-GFP was carried out as follows: After co-infection of AdAAV and AdrAAV-GFP into 293 cell, the cells were lysed by freezing and thawing three times and the viral supernatant heated to 56° C. for 1 hour. rAAV-GFP was then purified on a CsCl gradient. The purified rAAV-GFP was then incubated with an antibody (1D6.14, provided by Dr. Curiel, 33) capable of neutralization of adenovirus at 37° C. for 1 hour. The antibody-treated rAAV-GFP was inoculated into 293 cells at 10-fold serial dilutions, and the titer determined by counting the number of green cells at different dilutions 48 hour post-infection. The results were expressed as transduction units/cell (T.U./cell). The expression of rep and cap was monitored using Northern and Western blotting hybridization. To examine the efficiency of heat inactivation of AdrAAV-GFP, AdCMVGFP was also used as a control.

EXAMPLE 10
Attenuation of Rep Translation or Up-regulation of Cap in the Context of AdAAV Leads to Enhanced Production of rAAV-GFP AAV contains three promoters at map positions 5, 19, and 40 (the AAV genome corresponds to 100 map units) (26) which are used to regulate the expression of the two open reading frames. The p5 and p19 promoters direct expression of rep proteins 78, 68, 52 and 40. The p40 promoter drives capsid proteins VP1, VP2, and VP3. The rep proteins are key proteins for both the regulation of AAV gene expression and DNA replication. In the absence of helper virus, all four rep proteins negatively regulate p5 and p19 transcription (3, 38, 39). In the presence of helper virus, rep can transactivate transcription from all three AAV promoters (3, 21, 35, 38).

To enhance the production of rAAV, the translation efficiency of the AAV rep gene is attenuated or expression of the cap gene is up-regulated. Alternatively, an AdAAV virus is developed for separate expression of the cap and rep genes, so that the ratio of the cap gene product can be increased or decreased independently of rep expression.

Figure 8A:
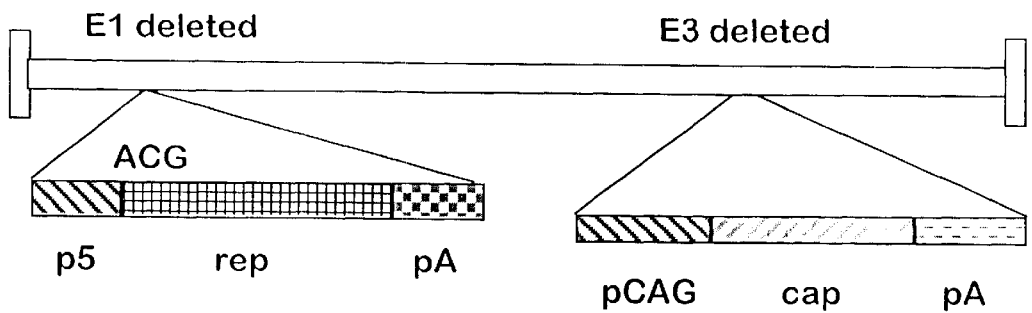
FIG. 8A shows construction of AdAAV with an attenuated translation start codon. The ATG start codon of rep was mutated into an ACG codon using PCR. The P40 promoter of the cap gene was replaced by the chicken β-actin promoter plus CMV enhancer (CAG start codon). The rep and cap expression cassette was inserted into E1 and E3 of pAdeasy1 by bacterial homologous DNA recombination. The resultant recombinant DNA was transfected into 293 cell to produce AdAAV.
Figure 8B:
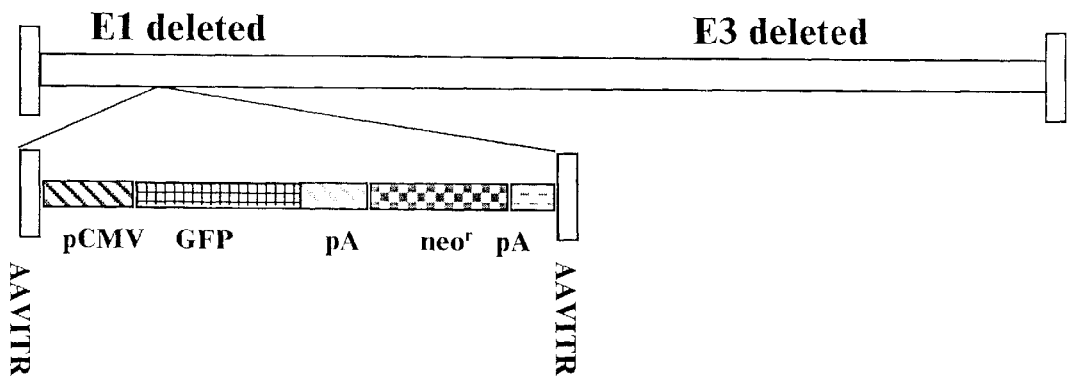
FIG. 8B shows construction of AdrAAV-GFP. AdrAAV-GFP was constructed as described in FIG.4A.

Attenuation of rep translation efficiency is carried out by changing the rep translation start codon from ATG to ACG in pShuttleAAV (FIG. 1), and then construction of the recombinant AdAAV expressing the rep gene with the ACG start codon (FIG. 8A). This codon change was shown to attenuate the translation efficiency of the rep gene. It is also possbile to enhance the AAV capsid protein expression by replacing the p40 promoter with the chicken β-actin promoter and the HCMV enhancer (which utilizes a CAG start codon) (FIG. 8A). Co-infection of this virus (FIG. 8A) with AdrAAV-GFP (FIG. 8B) results in high-titer production of rAAV-GFP. The production of rAAV-GFP is then evaluated under optimized viral dose conditions.

Figure 9A:
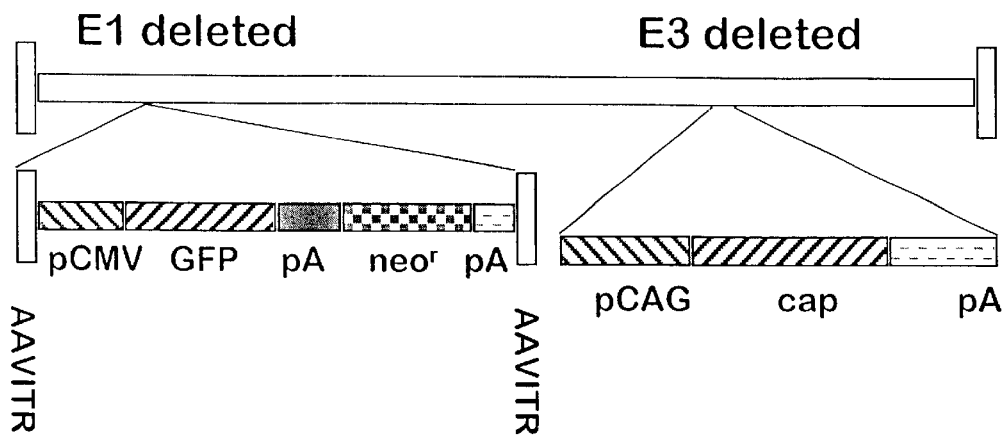
FIG. 9A shows construction of AdrAAV-GFPCap. The strategy used to construct AdrAAV-GFPCap was described in FIG. 8A, however the rep expression unit is replaced by a GFP expression unit using bacterial DNA homologous recombinant.
Figure 9B:
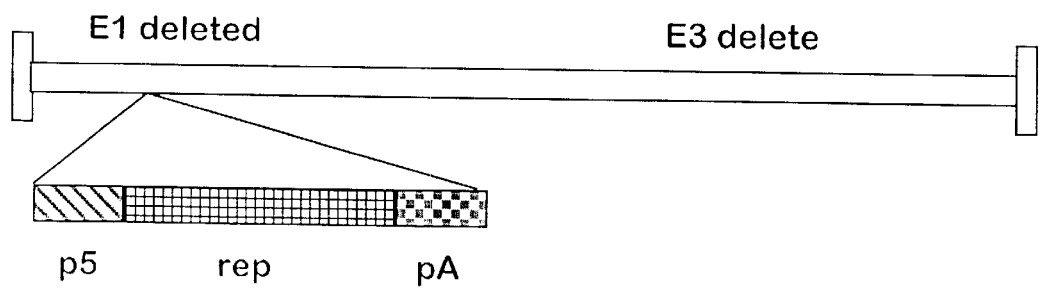
FIG. 9B shows the construction of recombinant AdrAAVrep virus. Rep expression unit was PCR-amplified and inserted into the BglII site of the pShuttle vector. The resultant plasmid was mixed with pAdeasy1 to generate pAdrAAVrep. pAdrAAVrep was then transfected into 293 cells to produce AdrAAVrep.

Alternatively, AdAAV viruses are developed that express the cap and rep genes separately so that it is possible to separately modulate the dose of the AAV rep or cap expression. Switching the rep gene with the GFP expression cassette results in the production of AdrAAV-GFPCap (FIG. 9A) and AdAAVrep (FIG. 9B) recombinant viruses. These two viruses are used to demonstrate that increasing the dose of AdrAAV-GFPCap while maintaining a constant level of rep expression significantly boosts the production of rAAV-GFP. By adjusting the time between addition of AdrAAV-GFPCap and AdAAVrep, the optimal conditions for maximizing production of rAAV-GFP are also determined.

EXAMPLE 11

Optimizing Conditions for Production of Ad-free rAAV-GFP

Although the method described in the present invention generates high titer and large scale production of rAAV-GFP using two recombinant viruses, minor contamination of Ad helper virus remains that is not acceptable for clinical applications. The Loxp/Cre system has been used to generate a recombinant adenovirus deleted of all coding sequences (30, 40). This strategy has also enabled other investigators to generate recombinant adenovirus with inserts up to 30 kb in length (30, 31, 41). However, the recombinant adenovirus preparations always have minor (0.1%) contamination of Ad helper virus (30). To eliminate this contamination, the Loxp/Cre system combined with thymydine kinase drug selection has been employed. In order to package the final recombinant adenovirus product (rAAV-Th), a helper adenovirus was additionally infected to provide the packaging functions for the recombinant adenovirus. This helper adenovirus was constructed such that the packaging sequence was flanked by two Loxp sites. Therefore, this virus can grow to high titer in 293 host cells, but not in 293 cells expressing Cre protein (293CreNS) which excises the adenoviral packaging signal. The minor helper Ad contamination was further eliminated using ganciclovir (GCV) drug selection. Ganciclovir is a good substrate for viral thymidine kinase but a weak substrate for the mammalian enzyme. Herpes simplex virus (HSV) thymydine kinase phosphorylates ganciclovir to the monophosphate form, which is then converted to the triphosphate form by cytoplasmic enzymes. Ganciclovir triphosphate, when incorporated into replicating DNA, stops chain elongation and results in cell death (42). Therefore, thymydine kinase drug selection kills cells infected with the AdLoxpTK helper virus, but not cells infected with recombinant AdrAAV8kb or AdrAAV-GFP8kb virus.

EXAMPLE 12

Ad-free rAAV-GFP was Produced Using an AdAAV Virus Deleted for Genes Essential for Ad in Combination with a Helper Virus Containing a Loxp-flanked Packaging Signal This strategy used two steps to produce Ad-free rAAV-GFP. First, AdAAV virus, with a deletion of the genes contained between the PmeI-SgfI fragment which are essential for Ad production, was produced with a conditional-packageable helper Ad with a Loxp flanked packaging signal (AdLoxpTK). These AdAAV were next used to co-infect 293CreNS cells to produce rAAV-GFP. However, a small fraction of cells produced AdLoxpTK resulting from contamination from the first step. Hence, the second step used the viral TK analogue, ganciclovir, to selectively kill these cells.

Figure 10A:
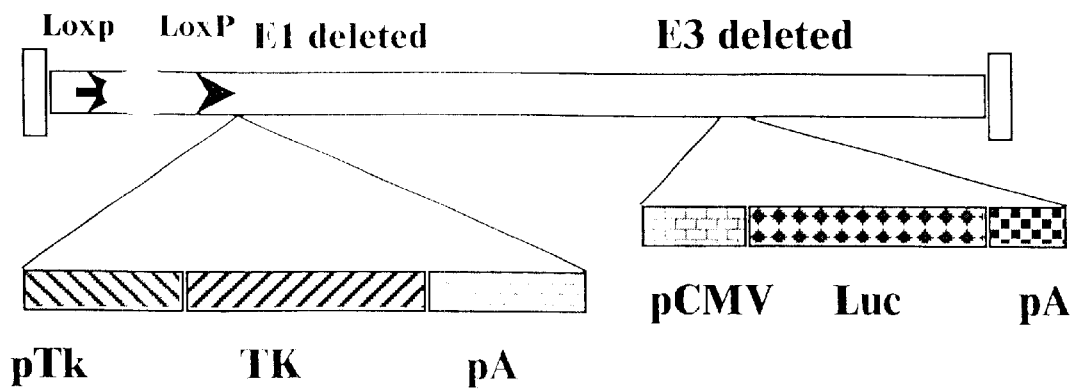
FIG. 10A shows construction of AdLoxpTK conditional-packageable helper virus. The Ad packaging sequencing flanked by two Loxp sites has been constructed by PCR technique (30). The luciferase gene has been inserted into pAdeasy1 E3 region. The HSVTK gene will be inserted into E1 region as described below.
Figure 10B:
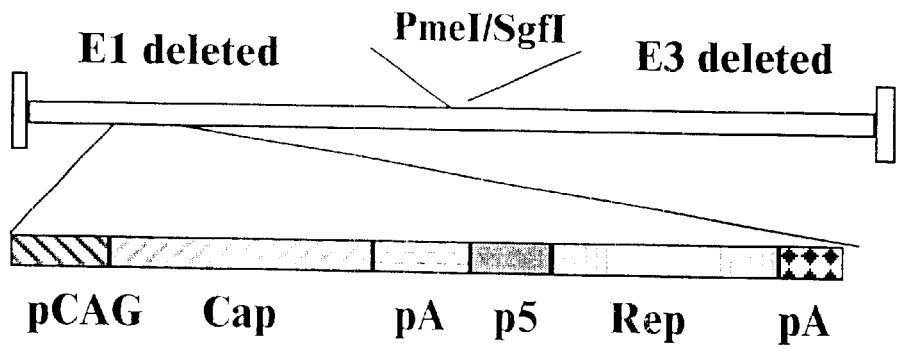
FIG. 10B shows the construction of recombinant AdrAAV8kb virus. The PmeI-SgfI fragment of pAdrAAV described in FIG. 1 was deleted to generate pAdrAAV8kb, followed by transfection into 293CreNS cells in the presence of AdLoxpTK. The recombinant AdrAAV8kb virus was purified through a CsCl gradient. The purified virus was titrated by dot-blotting followed by hybridization with an α-$^{32}$P labeled AAV cap gene probe.
Figure 10C:
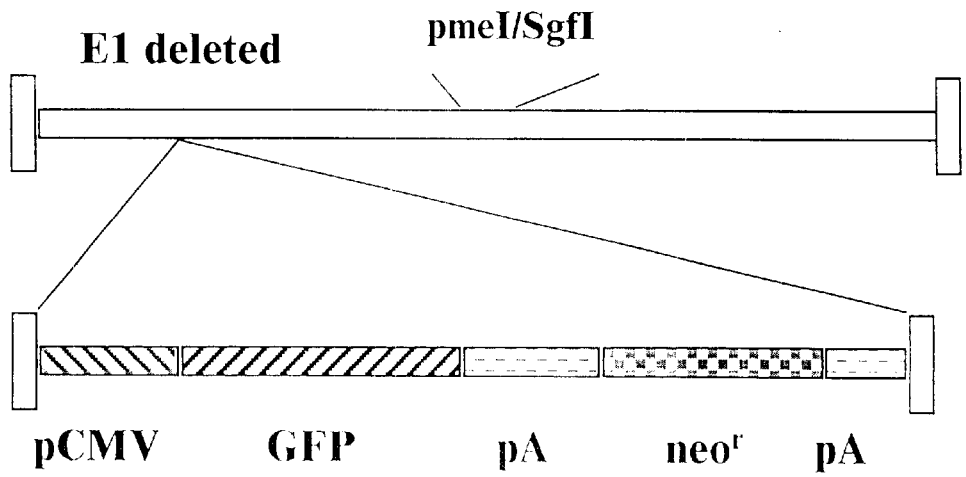
FIG. 10C shows the construction of recombinant AdrAAV-GFP8kb virus. The PmeI-SgfI fragment of pAdrAAV-GFP described in FIG. 4A was deleted to generate pAdrAAV-GFP8kb, followed by transfection into 293CreNS cells in the presence of the AdLoxpTK virus. The recombinant AdrAAV-GFP8kb was purified through a CsCl gradient. The virus was titrated using dot-blotting followed by hybridization with an α-$^{32}$P GFP probe.

The Loxp/Cre system was first used to generate a conditional-packageable Ad helper adenovirus expressing the HSV TK gene (FIG. 10A). The helper virus, AdLoxpTK, will not be packaged in 293CreNS cells, but will be fully functional and provide packaging function for the helper dependent recombinant adenovirus. To generate the AdLoxpTK recombinant virus, the BamHI fragment containing the HSVTK expression unit (BRL) was inserted into the BglII site of the pShuttleLoxp plasmid (32), followed by co-transformation with pAdeasy1 into bacterial BJ5183 to allow in vitro recombination. After selection, the correct recombinant DNA was linearized with PacI, and then transfected into 293 cell to generate the AdLoxpTK virus. The helper-dependent recombinant adenoviruses, including AdrAAV8kb (FIG. 10B) and AdrAAV-GFP8kb (FIG. 10C) which produces high-titer, Ad-free rAAV, was constructed by deleting an 8 Kb PmeI-SgfI fragment encoding the Ad hexon, penton, core protein, and DNA polymerase genes from plasmid pAdAAV or pAdrAAV-GFP (FIG. 1A, FIG. 4A). This virus already has deletions in the E1 and E3 genes. Both constructs are able to replicate and be packaged in the presence of the Ad helper virus, AdLoxpTK, in 293CreNS cells. After CsCl purification, the viruses were infected into 293NSCre cells to demonstrate that high titer Ad-free rAAV-GFP can be produced in the presence of the TK analogue, ganciclovir, which selectively kills the AdLoxpTK helper virus.

To maximize production of Ad-free rAAV-GFP, optimization of timing and dose of both recombinant viruses was carried out and the titer of generated rAAV-GFP determined. The degree of Ad-free rAAV-GFP was evaluated both in vitro and in vivo. In vitro, CsCl purified rAAV-GFP was used to infect 293 cells and the amount of Ad helper contamination evaluated by quantitation of luciferase expression (28) and PCR amplification of the luciferase gene. Because a recombinant adenovirus can cause a strong immune response, but rAAV does not (43, 44), the purity of Ad-free rAAV-GFP was evaluated as follows. $1 \times 10^{10}$ T.U. of rAAV-GFP was intravenously injected into C57BL/6−+/+ mice and evaluated at day 7, 30, 50, and 100 to examine potential inflammatory response, the level of GFP expression, T cell cytotoxicity and antibody resposne to AAV, Ad, and GFP. In addition, luciferase gene was PCR-amplified to detect the amount of AdLoxpTK contamination.

EXAMPLE 13

Ad-free rAAV-GFP was Produced Using a Single AdAAV

The preceding experiments determined the feasibility of producing high yield Ad-free rAAV-GFP. This requires co-infection with two AdAAVs at optimal ratios for production of the rAAVs. Since the procedure is now established using two viruses, it is advantageous to combine these features into a single AdAAV.

Figure 11:
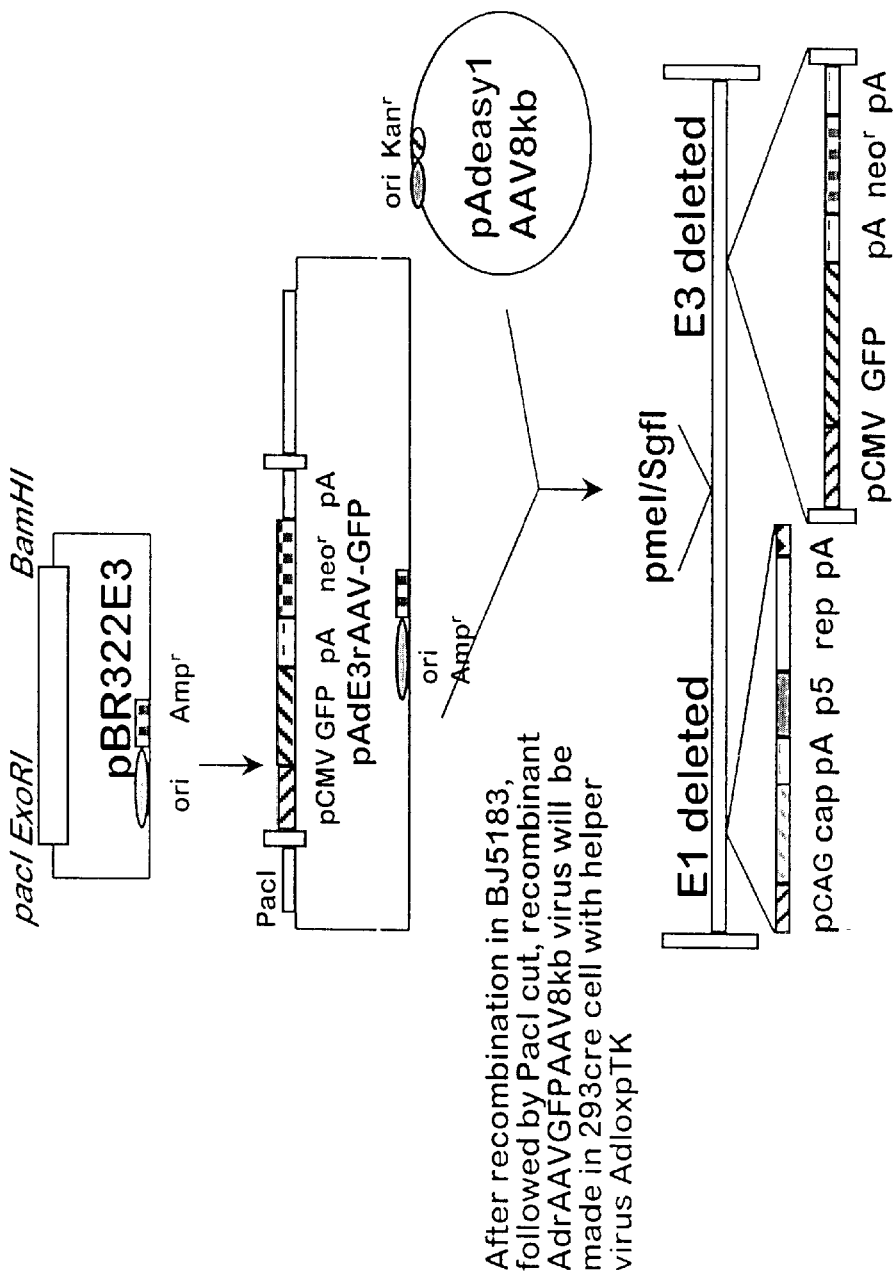
FIG. 11 shows the construction of AdrAAVGFPAAV8kb. The AdrAAVGFPAAV8kb was constructed as described in the examples. The first step was to construct pAdE3rAAV-GFP, which was then combined with pAdrAAV8kb (described in FIG. 10B) and resulted in pAdrAAVGFPAAV8kb. Transfection into 293NSCre in the present of AdLoxpTK generated AdrAAVGFPAAV8kb recombinant virus.

To achieve large scale production of rAAV at low cost, a single recombinant cassette is constructed to generate rAAV-GFP. First, the 12-kb PacI-BamHI fragment containing the E3 deleted region is isolated from pAdeasy1 and cloned into pBR322 with a PacI adaptor. A BglII fragment from pAdrAAV-GFP containing GFP flanked by AAV ITR is blunt-end ligated into the EcoRI site and klenow filled-in to create the resultant plasmid, pAdE3rAAV-GFP (FIG. 11), located within E3. After linearization with PacI, the pAdE3rAAV-GFP is co-transformed with pAdrAAV8kb (as described in FIG. 10B) to allow in vitro recombination in the BJ5183 host cells. The resultant recombinant plasmid DNA, pAdrAAVGFPAAV8kb, is transfected into 293CreNS cells to make recombinant virus in the presence of conditional packageable AdLoxpTK helper virus, as shown in FIG. 10A.

The level of production of Ad-free rAAV-GFP is examined after harvesting 293CreNS infected with AdrAAVGFPAAV8kb in the presence of the TK analogue, ganciclovir. The purity of rAAV-GFP is evaluated both in vitro and in vivo. In vitro, CsCl purified rAAV-GFP is used to infect 293 cells and the degree of Ad helper contamination is evaluated by quantitation of luciferase expression (28) and PCR. In vivo, $1 \times 10^{10}$ T.U. of rAAV-GFP is intravenously injected into C57BL/6−+/+mice. The mice are evaluated at day 7, 30, 50, and 100 to examine potential inflammatory response, the level of GFP expression, T cell cytotoxicity and antibody response to AAV, Ad, and GFP.

Summary rAAV titer can be increased by using the following strategies: a) increasing the dose of, or pre-infection with, Ad helper virus (8); b) down-modulation of rep translation efficiency or increasing cap expression (8, 11); c) using non-replicative Ad helper DNA instead of infectious adenovirus (4, 6, 7); and d) use of a stable cell line which constitutively expresses the rep and cap genes to provide rAAV packaging function (16, 17).

However, previous methods have used a low efficiency and expensive DNA transfection strategy. To overcome this problem, the present invention utilized recombination in bacteria to generate two recombinant plasmid vectors in vitro (e.g., pAdAAV and pAdrAAV-GFP). One plasmid expresses the AAV rep and cap genes (e.g., pAdAAV), the other expresses GFP flanked by AAV ITR (e.g., pAdrAAV-GFP). These plasmids can be directly transfected into host cells to produce recombinant viruses (e.g., AdAAV and AdrAAV-GFP). This novel strategy will allow optimized production of rAAV (e.g., rAAV-GFP).

EXAMPLE 14
Evaluation of Capsid Expression by AdAAV

Figure 12A:
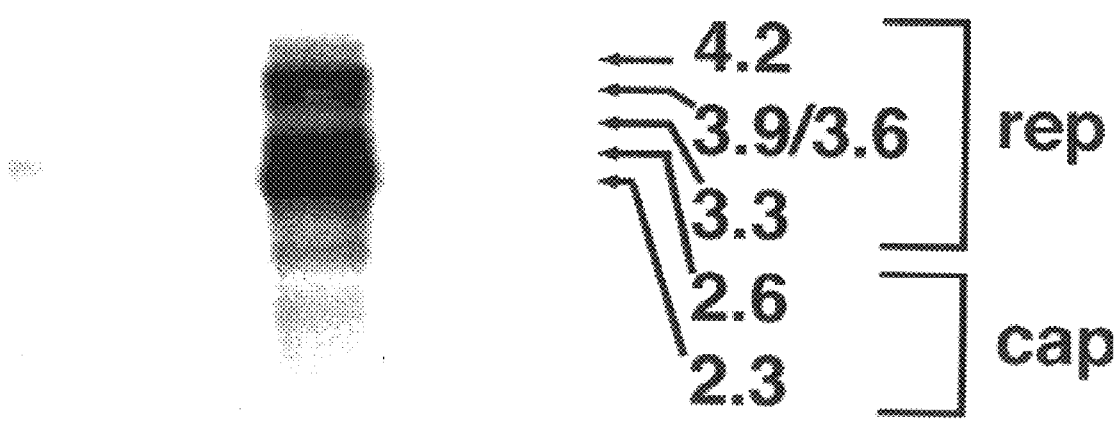
FIG. 12A shows a Northern blot of AdAAV RNA probed with reps and caps. Lanes: 1, RNA marker; 2, cell RNA; 3, AdAAV RNA; 4, AdLacZ RNA.
Figure 12B:
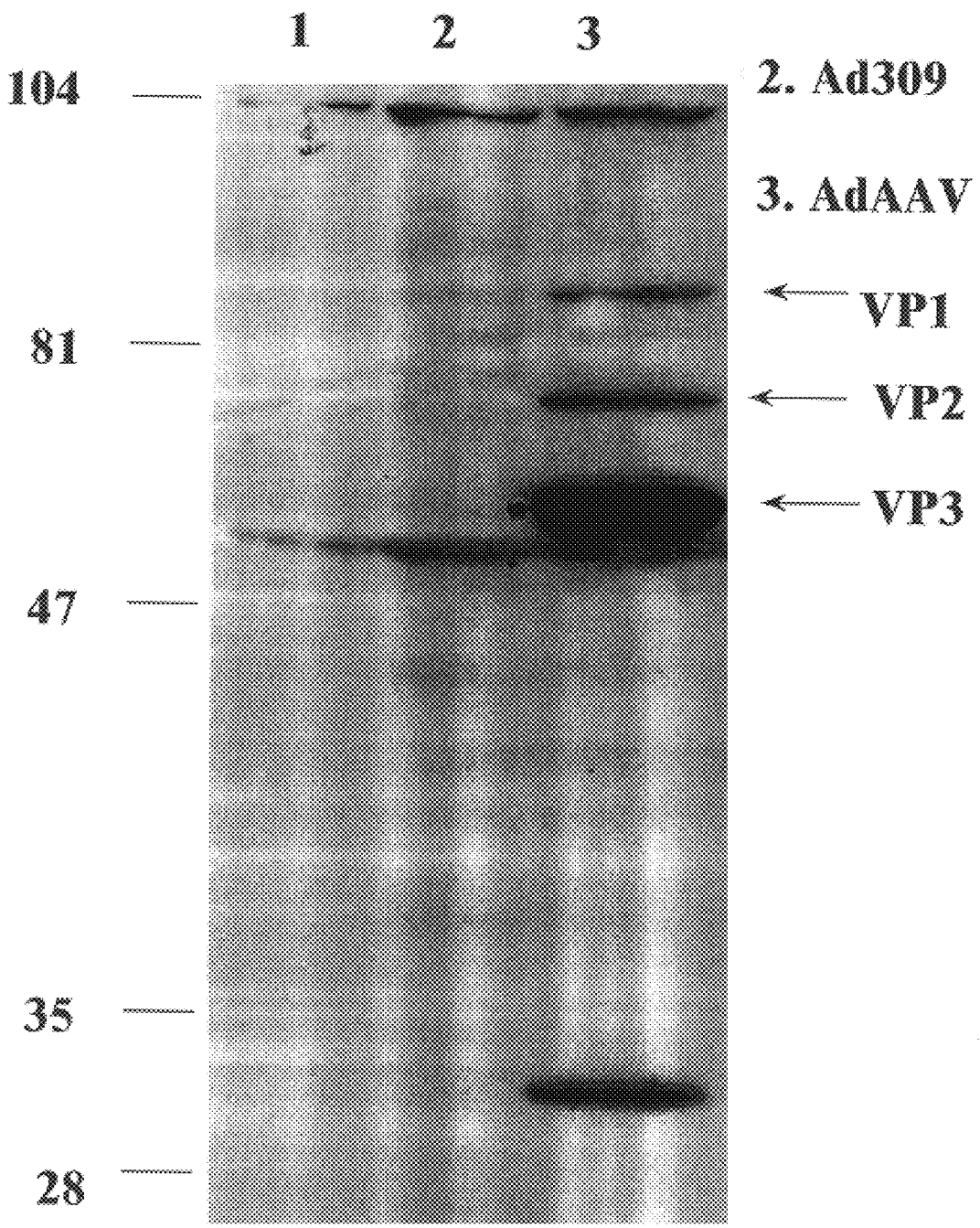
FIG. 12B shows a Western blot of AAV capsid proteins produced 24 hours after transfection of 293 cells with AdAAV. 50 μg total protein was loaded in each lane.

To demonstrate that AdAAV produced viable recombinant adeno-associated virus particles (AAV), GFP expression was detected following co-infection of AdrAAV-GFP and AdAAV into 293 cells. To further demonstrate that normal AAV capsid proteins are produced, 293 cells were transfected with the AdAAV construct. After 24 hours, the protein from the cells was obtained. As a control, 293 cells either remained uninfected or were infected with wild type Ad309 virus. 50 µg of total protein was electrophoresed and blotted onto nitrocellulose. The expression of AAV capsid proteins was examined using a mouse monoclonal antibody (clone B1) that reacts to free VP1, VP2 and VP3 of the adeno-associated virus (American Research Products, Inc., Belmont, Mass.). There was high expression of the three capsid proteins using this anti-VP1, VP2 and VP3 antibody. These are represented by the bands marked as VP1 at approximately 90 Kd, VP2 at approximately 78 Kd and the intense band marked as VP3 at approximately 57 Kd (FIG. 12). These result indicate that AdAAV can induce high titer rAAV expression within 24 hours after transfection into 293 cells based upon high expression of the cap genes.

Figure 13:
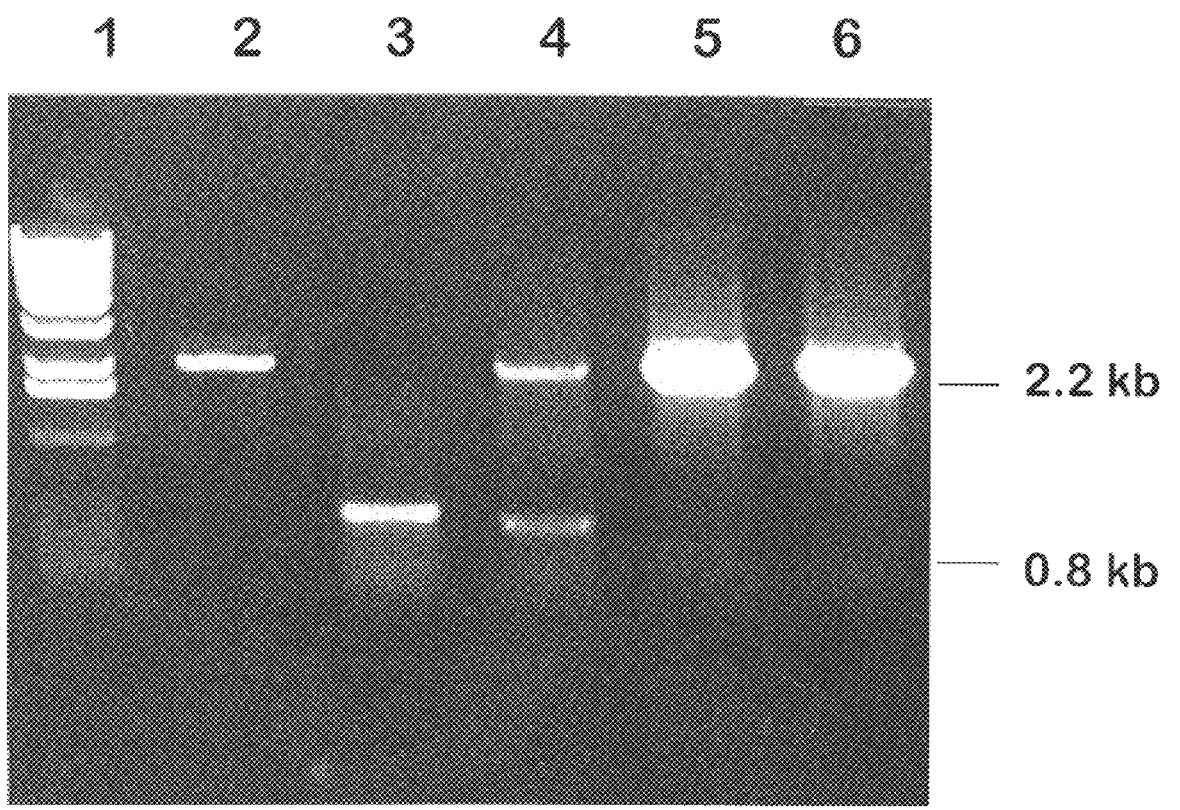
FIG. 13 shows that the rep genes within the AdAAV genome are unstable. Using primers specific for the Ad region flanking the rep genes, the full-length wildtype rep genes amplifies a 2.2 Kb fragment, while a deletion within the rep genes occurs following multiple passages through 293 cells. Lane 1, 1 Kb marker; Lane 2, AdAAV, 1 passage; Lane 3, AdAAV, 8 passages; Lane 4, AdAAV, 4 passages; Lane 5, AdAAV plasmid; Lane 6, AdAAV plasmid, AAV and helper phage.

EXAMPLE 15
Identification of a Deletion in the Rep Gene After Passage of AdAAV in 293 Cells The production of high titer AdAAV within 24 hours demonstrates high-titer production of rAAV using this chimeric vector. To determine the etiology of the previously reported inability to express the AAV rep proteins in the context of an AdAAV chimeric vector, the AdAAV vector was passed through 293 cells for one passage, four passages and eight passages. The DNA was isolated after each passage and primer sequences were designed to the adenovirus vector sequences that flank the incorporated AAV in the AdAAV virus, specifically those sequences flanking the rep genes. Using these primers, the genomic integrity of the AAV insert after different numbers of passage wag examined (FIG. 13). After one passage, the full-length (2.2 Kb) rep genes were incorporated into the AdAAV chimeric vector (lane 2), and were identical in size to the wildtype rep genes (lanes 5 and 6). After four passages, there was an appearance of a truncated, approximately 0.8 Kb rep gene incorporated into the AdAAV chimeric vector, however the majority of AdAAV contained a full-length 2.2 Kb fragment. At eight passages (lane 3), most of the AdAAV vectors exhibited a deletion within the rep genes. These results demonstrate that upon extended passage of the AdAAV chimeric vector, a portion of the rep gene is excised.

EXAMPLE 16
Deletion of the Rep Gene is not Site Specific

The PCR products representing the deleted rep genes in AdAAV after 8 passages through 293 cells were cloned and sequenced. The deletion always occurred within the rep sequence of AAV (FIG. 14), however, the deletion was not site-specific. The entire rep gene is approximately 2.2 Kb, which encodes rep78, rep68, rep52 and rep40. The deletions that occurred in the rep gene after high passage of the AdAAV chimeric vector were sufficient to disrupt all four rep genes, however, the deletions were not in the same site in any of the three clones examined. The 2.2 Kb rep genes are represented as map units 0.5 to 52. Deletion #1 was between map unit 10 and map unit 40; deletion #2 was between map unit 15 and map unit 45; and deletion #3 was between map unit 20 and map unit 30. These results indicate first, that after numerous passages, all deletions within AAV are within the rep genes, and second, that the deletions do not occur at a specific site, but the deletion are such that they incapacitate all of the rep proteins.

EXAMPLE 17
Description of an Ad-minigene to Limit the Deletion of the Rep Genes in AdAAV After Multiple Passages The adenovirus genes E1A, E1B, E2A, E4 and VAI RNA are essential for AAV replication. An Ad-minigene plasmid containing those essential genes was produced and used for replication of AAV. This minigene has several advantages over using the entire Ad genome to induce AAV replication. First, the function of several of these essential genes are known. For example, E1A is known to induce replication and may contribute to second strand synthesis of the rAAV ss DNA. Second, use of this Ad-minigene eliminates the Ad gene(s) responsible for deletion within the rep genes. Third, elimination of Ad genes, e.g. fiber, reduces competition with transcription machinery.

EXAMPLE 18
Production of a Mini-AdAAV Vector

A mini-AdAAV allows high titer and multiple passages with reduced frequence of deletion. This construct contains all the Ad genes necessary for AAV replication, but does not contain the gene(s) responsible for deletion of the AAV rep gene. The mini-AdAAV also enables second strand synthesis and replication of AAV in vivo.

As stated above, the adenovirus genes necessary for AAV replication include E1A, E1B, E2A, E4 and VAI RNA. The mini-AdAAV vector contains these essential genes, as well as the AAV rep and cap genes and the Ad packaging signal, all of which are flanked by the Ad ITR as shown in FIG.

15A. The mini-AdAAV vector is produced in the 293/Cre cell line using an Ad helper virus that expresses only the essential genes. The helper virus is eliminated by the Loxp/Cre system described above. Therefore, the combination of these essential genes, along with the AAV cap and rep genes, result in production of a stable AdAAV that is packaged and undergoes multiple passages without deletion of the rep gene.

EXAMPLE 19
A Method for in vivo Amplification of rAAV-GFP

One limitation to gene therapy is that the current vectors cannot be amplified in vivo. For example, in vivo amplification is highly efficacious and/or necessary for treatment of cancer with pro-apoptotic genes, since 100% of cancer cells would presumably need to be transfected with the therapeutic vector. In vivo amplification enables a high level of transfection to occur. In vivo amplification is safely carried out using the AAV vector since AAV is not a pathogenic virus and approximately 90% percent of the population has been infected with AAV. Therefore, in vivo amplification of this gene therapy vector is safe.

In vivo amplification is achieved using the mini-AdAAV vector in combination with a recombinant AAV vector containing a transgene (e.g., rAAV-GFP). The mini-AdAAV vector is an adenovirus that has extensive deletion of unnecessary genes but contains the genes required for AAV growth. In addition, it contains an AAV rep and cap gene (FIG. 15B). The mini-AdAAV vector requires co-infection with recombinant AAV containing the therapeutic gene.

A therapeutic AdrAAV chimeric vector is identical to the mini-AdAAV vector except that the therapeutic AdAAV chimeric vector also includes the AAV-ITR which flanks a therapeutic gene (FIG. 15B). For example, green fluorescent protein (GFP) is used as a marker instead of a therapeutic gene. For cancer therapy, apoptosis genes including, but not limited to, p53, Bax, Bid, Bad, IkB-dominant negative, antisense-XIAP, dominant mutant Akt, and PTEN, are used. The advantage of the second chimeric vector is that only a single virus is required, which contains both essential adenovirus sequences, AAV rep and cap genes and the recombinant AAV carrying a therapeutic gene.

EXAMPLE 20
Method for Modified Tropism of AdAAV

Figure 16:
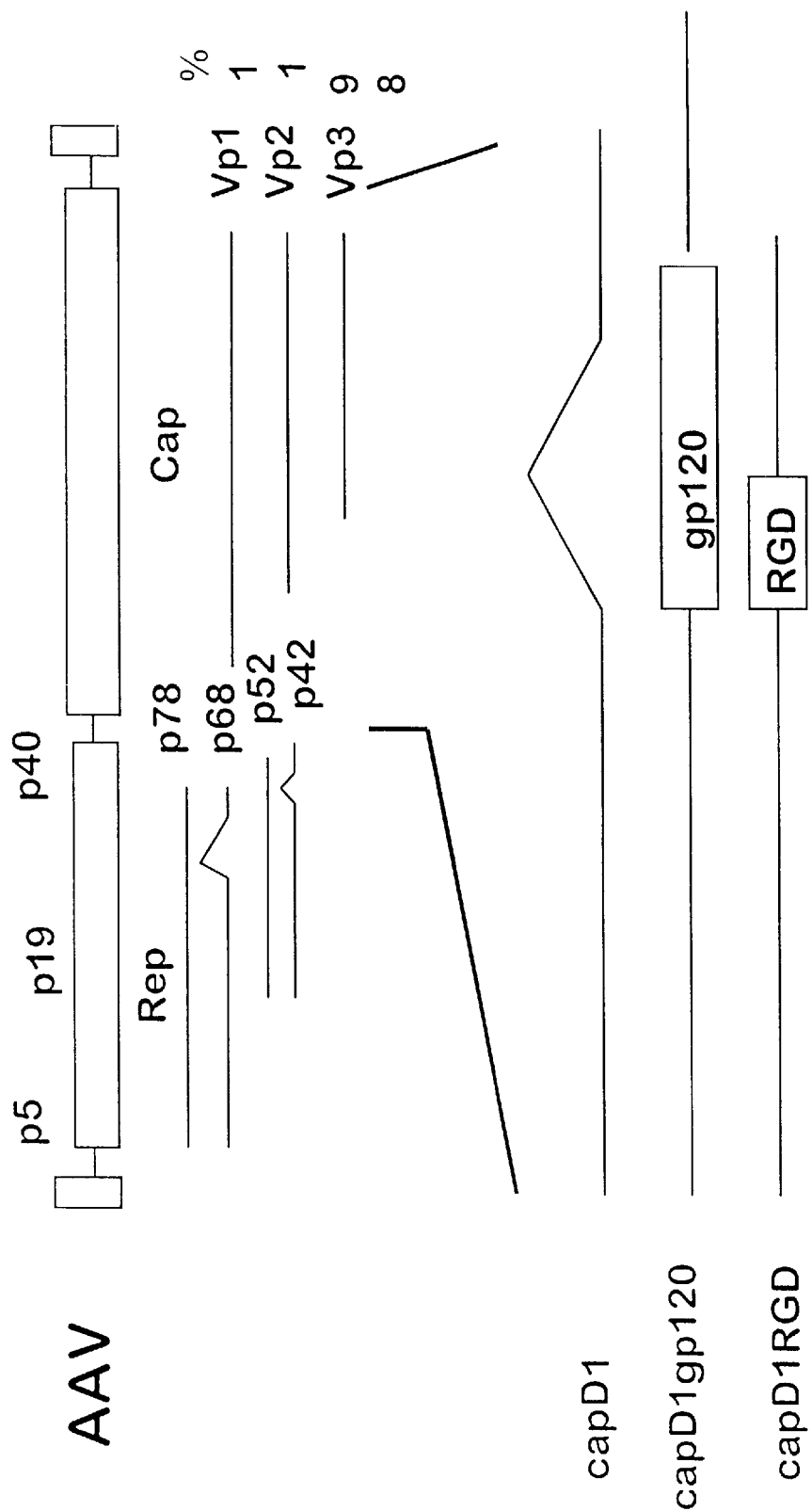
FIG. 16 shows constructs in which the cap gene has been deleted and replaced with the gp120 gene from the HIV virus or sequences encoding an RGD binding peptide.

A region of the AAV VP3 cap gene between residues 285 (Q) and 357 (I) was deleted and a viable AAV produced (FIG. 16). This was demonstrated by visualization of a Cap gene mutant rAAV-GFP in a 293 cell line. Altered tropism could be conferred to rAAV-GFP by replacing AAV VP3-deleted region with the V3 portion of the gp120 HIV virus coding region. This resulted in increased tropism to T cells. A second modification cloned the RGD binding peptide into this region, resulting in increased binding to RGD sequences.

Figure 14:
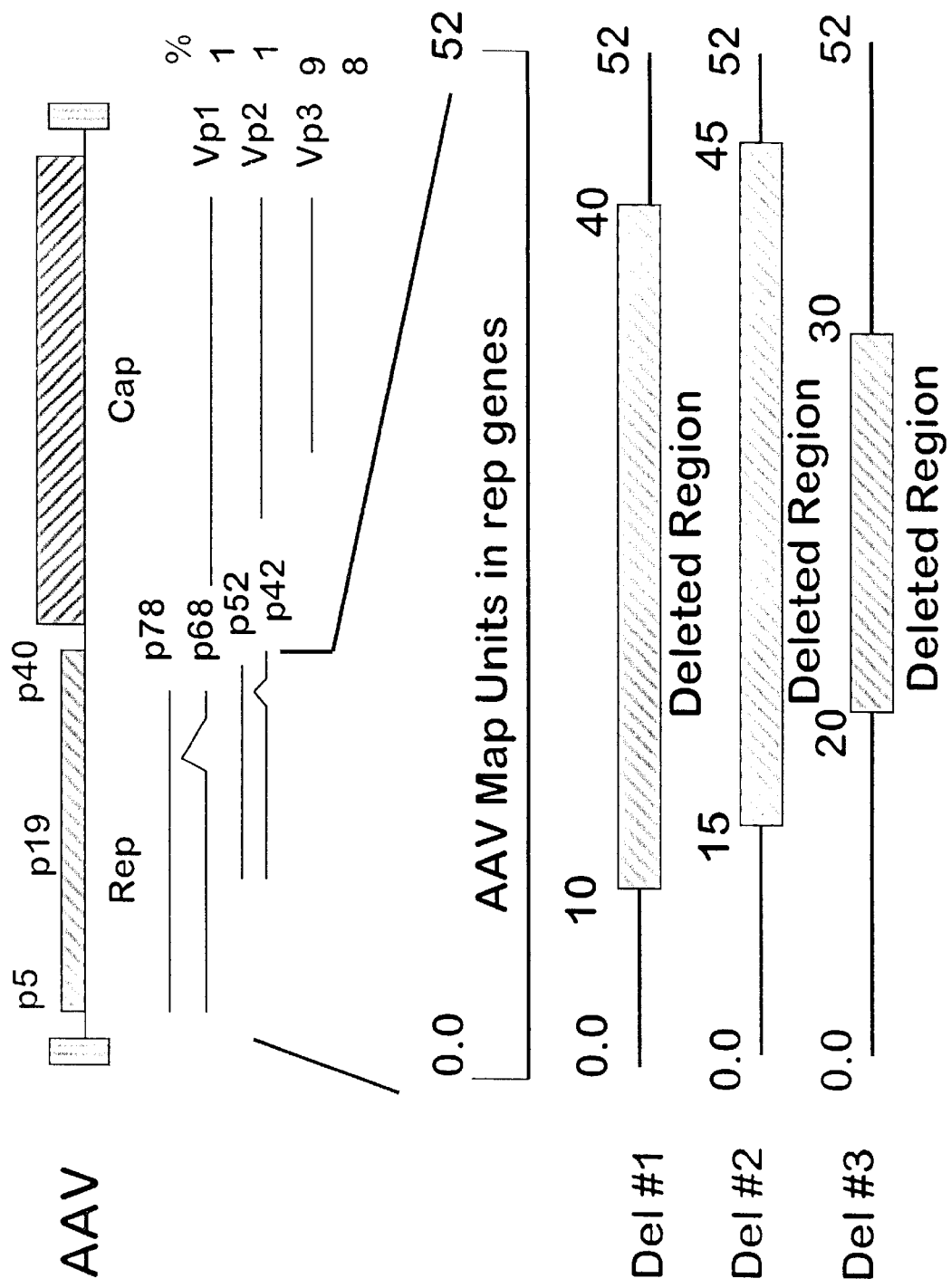
FIG. 14 shows characterization of the three clones carrying deletions in the rep genes relative to map units.
Figure 15:
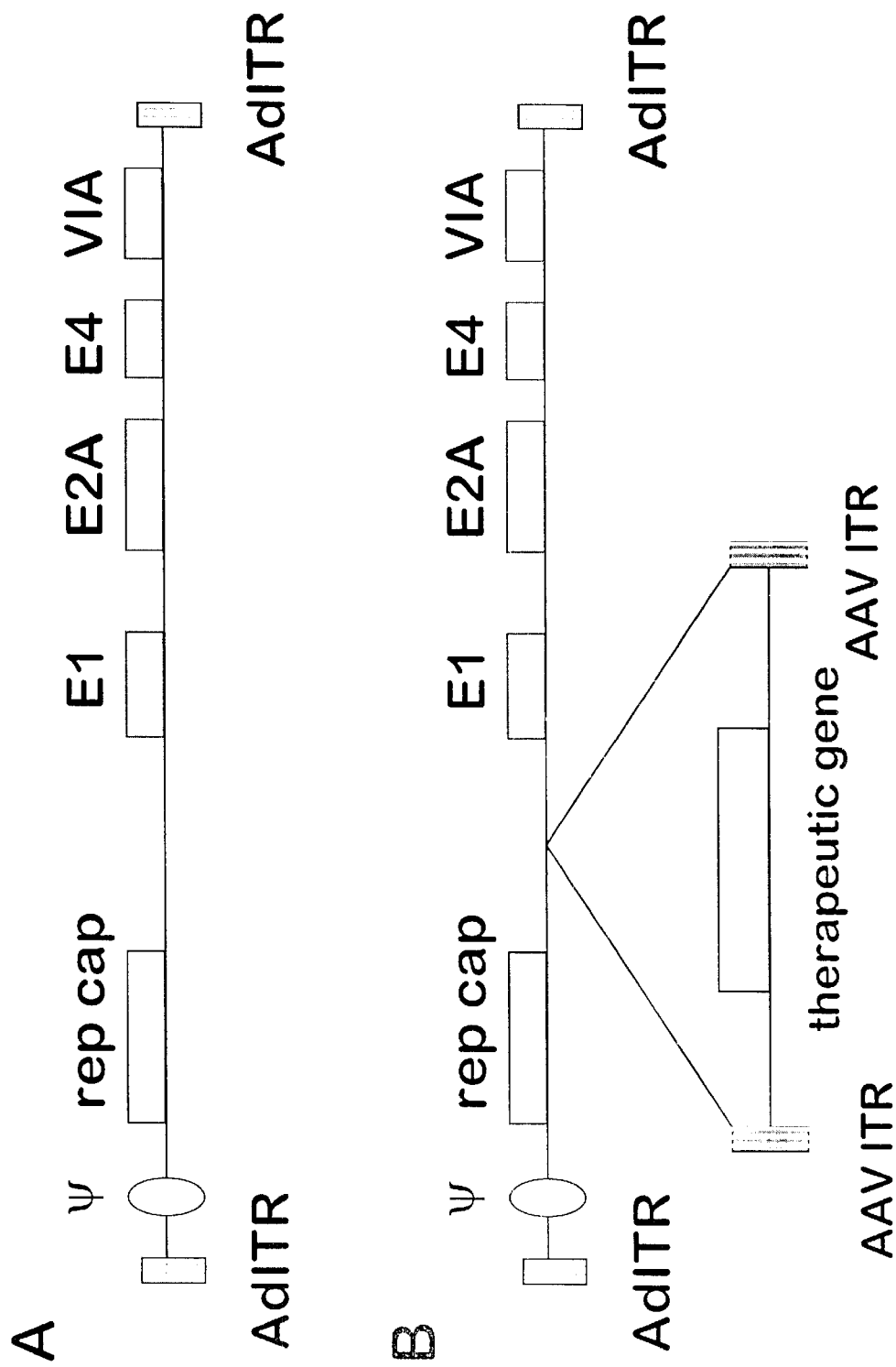
FIG. 15 shows schematics of two of the vectors described herein, the mini-AdAAV vector (top) and the therapeutic AdAAV vector (bottom).

The present invention demonstrates that: (1) recombinant Ad with AAV rep and cap, can be combined within a single AdAAV construct. This is referred to as AdAAV and is distinct from previous descriptions of recombinant AAVs (rAAV) that have been cloned into the E1 site of Ad. Previous AdrAAV do not contain the full length AAV rep and cap in the E1 site of Ad; (2) circularized wild type Ad can not be packaged, but helps to linearize AdAAV to initiate replication, followed by packaging; (3) this AdAAV can be grown to a high titer of $10^{10}$ AdAAV particles/ml; (4) AdAAV can be used to transfect 293 cells with high efficiency and avoids the need for transfections with multiple plasmids; (5) transfection results in production of a viable recombinant AAV that expresses GFP (rAAV-GFP), and can therefore be used to express a therapeutic gene; (6) the high titer AAV produces high levels of cap RNA and protein, as well as high levels of rep RNA and protein (FIG. 12); (7) the production of AdAAV has enabled the identification of the nature of the interference or inhibitory effect of Ad and AAV when grown together. Continuous passage of the AdAAV through 293 cells lead to deletion of approximately 1.4 to 0.8 kB of the rep gene, which results in the observed inhibitory effect between Ad and AAV (FIG. 13); (8) the deletion was analyzed in 3 different recombinants and is not site specific; (9) the deletion requires Ad genes that are not essential for AAV replication, since transfection with an Ad mini-gene plasmid containing only genes essential for AAV replication does not result in deletion within the AAV rep gene. (FIG. 14); (10) production of a mini-AdAAV with deletion of the Ad gene, which leads to deletion within the AAV rep gene, can be used to produce a stable mini-AdAAV; (11) the Ad genes contained within the mini-AdAAV are sufficient to enable second strand synthesis, and therefore, are sufficient to enable in vivo replication of the single stranded rAAV; (12) the stable mini-AdAAV will enable replication of a stable rAAV-GFP in vivo. Stable in vivo replication of rAAV-GFP is useful for high in vivo amplification of rAAV-GFP and high infection of cells. This method of high titer rAAV-GFP production is likely to deliver the desired therapeutic gene to a high percentage, if not all cells, to ultimately correct a genetic defect or to impart a new genetically-transferred property to certain cells. This includes, but is not limited to, high efficiency transfection of cancer cells with genes directing and/or regulating apoptosis, including Bax, Bad, IkB-DN, FasL, Akt and others (FIG. 15); (13) the region of the AAV capsid was identified that can be deleted without preventing the production of viable rAAV (FIG. 16); (14) the capsid region can be mutated by replacement with sequences that alter the tropism of AAV, and production of high titer rAAV is still enabled, (15) modifications to this region in the AAV capsid by replacement with a sequence of the CD4 binding domain of the gp120 AIDS capsid result in increased tropism to T cells. Insertion of an RGD sequence can increase tropism to RGD binding sequences (FIG. 16); and (16) modification of the AAV capsid in the mini-AdAAV enables local amplification of an rAAV-GFP with altered tropism. This is applicable, but not limited, to delivery of genes that direct and/or regulate apoptosis to tumor cells using tumor antigens or receptors that are recognized by the altered AAV capsid. This targeted approach enables higher local amplification in a limited tissue type, such as tumor tissue, with reduced infection of surrounding or distant normal tissue that does not express the specific tumor antigen.

The following references were cited herein:
1. Fisher, K. J., et al. 1996. Hum. Gene Ther. 7:2079–2087.
2. Casto, B. C., et al. 1967. Virology 32, 52–59.
3. Carter, B. J., et al. 1979. Virology 92, 449–462.
4. Ferrari, F. K., et al. 1997. Nat. Med. 3:1295–1297.
5. Ferrari, F. K., et al. 1996. J. Virol. 70:3227–3234. 39.
6. Salvetti A, et al. 1997. Factors influencing recombinant adeno-associated virus production. Laboratoire de Therapie Genique, CHU Hotel-DIEU, Nantes, France.
7. Xiao X, et al. 1998. Virol 72(3):2224–2232.
8. Weger S, et al. 1997. J Virol 71(11):8437–8447.
9. Ogasawara Y, et al. 1998. Microbiol Immunol 42(3): 177–185.
10. Urcelay, E., P. et al. 1995. J. Virol. 69:2038–2046.
11. Li, J., et al. 1997. J. Virol. 71:5236–5243.
12. Samulski, R. J., et al. 1989. J. Virol. 63:3822–3822.

13. Samulski, R. J., et al. 1987. J. Virol. 61:3096–3101.
14. Muzyczka, N. 1992. Curr. Top. Microbiol. Immunol. 158:97–129.
15. Flotte, T. R., et al. 1995. Gene Ther. 2:29–37.
16. Clark, K. R., et al. 1995. Hum. Gene Ther. 6:1329–1341.
17. Clark, K. R., et al. 1996. Gene Ther. 3:1124–1132.
18. Carter, B. J. 1996. Nat. Biotechnol. 14:1725–1727.
19. Verma, I. M., and N. Somia. 1997. Nature 389:239–242.
20. Kotin, R. M. 1994. Hum. Gene Ther. 5:793–801.
21. Vincent, K. A., et al. 1997. J. Virol. 71:1897–1905.
22. Chang L S, et al. 1989. J Virol 63(8):3479–3488.
23. Chang L S, and Shenk T. 1990. J Virol 64(5):2103–2109.
24. Laughlin, C. A., et al. 1982. J. Virol. 41: 868–876.
25. Trempe, J. P., and B. J. Carter. 1988. J. Virol. 62:68–74.
26. Berns, K. I. 1996. Parvoviridae: the viruses and their replication, p. 2173–2197. IN B. N. Fields, D. M. Knipe, and P. M. Howley (ed.), Fields virology, 3rd ed., vol. 2. Lippincott-Raven, Philadelphia, Pa.
27. Fukushige S, and Sauer B. 1992. Proc Natl Acad Sci USA 1;89(17):7905–7909.
28. Zhang H G, et al. 1998. J Virol 72(3):2483–2490.
29. Lieber A, et al. 1997. Nat Biotechnol 15(13):1383–1387.
30. Parks R J, et al. 1996. Proc Natl Acad Sci USA 26;93(24):13565–13570.
31. Parks R J, and Graham F L. 1997. J Virol 71(4): 3293–3298.
32. He T C, et al. 1998. Proc Natl Acad Sci USA 3;95(5): 2509–298.
33. Douglas et al. 1997. Neuromuscul Disord 7(5):284–298.
34. Hirt, B. 1967. J. Mol. Biol. 26: 365–369.
35. Kotin, R. M., et al. 1990. Proc. Natl. Acad. Sci. USA.
36. Srivastava, A. 1994. Blood Cells 20:531–536.
37. Pereira, D. J., et al. 1997. J. Virol. 71:1079–1088.
38. Fisher, K. J., et al. 1996. J. Virol. 70:520–532.
39. Wang X S, and A. Srivastava. 1998. J Virol 72(6): 4811–4818.
40. Schiedner G, et al. 1998. Nat Genet 18(2):180–183.
41. Floyd S S Jr, et al. 1998. Gene Ther 5(1):19–30.
42. Yang L, et al. 1998. Clin Cancer Res 4(3):731–741.
43. Jooss K, et al. 1998. Gene Ther 5(3):309–319.
44. Jooss K, et al. 1998. J Virol 72(5):4212–4223.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of producing recombinant adeno-associated virus (AAV) comprising a foreign gene, comprising the steps of:
   a) infecting cells with:
      (i) a recombinant helper adenovirus comprising adeno-associated virus rep and cap genes and an adenovirus genome deleted of coding sequences other than those genes required for AAV replication; and
      (ii) a recombinant adenovirus comprising a foreign gene, wherein said foreign gene is flanked by AAV inverted terminal repeat ends;
   b) purifying and titering viral particles from said cells, wherein said viral particles comprise recombinant adeno-associated virus comprising said foreign gene.

2. The method of claim 1, wherein said cells are selected from the group consisting of 293 cells and 911 cells.

3. The method of claim 1, wherein said foreign gene is selected from the group consisting of an HSV-TK gene, a gene encoding GFP and genes encoding proteins that direct and/or regulate apoptosis.

4. The method of claim 3, wherein said genes encoding proteins that direct and/or regulate apoptosis are selected from the group consisting of Bax, Bad, IKB-DN, FasL and Akt.

5. The method of claim 1, wherein translation of said AAV rep gene is attenuated.

6. The method of claim 5, it wherein said rep gene is attenuated by changing the start codon of said gene.

7. The method of claim 6, wherein said start codon is changed from ATG to ACG.

8. The method of claim 1, wherein expression of said AAV cap gene is increased over endogenous levels.

9. The method of claim 8, wherein the expression of said AAV cap gene is increased by replacing a promoter directing expression of said gene.

10. The method of claim 1, wherein said AAV gene encoding said cap protein is engineered such that said recombinant AAV comprising a foreign gene is targeted to a specific cell type expressing a specific ligand.

11. The method of claim 10, wherein said ligand is selected from the group consisting of a CD4 binding domain and an RGD binding motif.

* * * * *